(12) United States Patent
Emig et al.

(10) Patent No.: US 10,858,649 B2
(45) Date of Patent: Dec. 8, 2020

(54) IMMUNE REPERTOIRE SEQUENCE AMPLIFICATION METHODS AND APPLICATIONS

(71) Applicant: Augmenta Bioworks, Inc., Menlo Park, CA (US)

(72) Inventors: Christopher J. Emig, Menlo Park, CA (US); Marco Mena, Sunnyvale, CA (US)

(73) Assignee: Augmenta Bioworks, Inc., Menlo Park, CA (US)

(*) Notice: Subject to any disclaimer, the term of this patent is extended or adjusted under 35 U.S.C. 154(b) by 336 days.

(21) Appl. No.: 15/704,619

(22) Filed: Sep. 14, 2017

(65) Prior Publication Data
US 2018/0073014 A1 Mar. 15, 2018

Related U.S. Application Data

(60) Provisional application No. 62/395,241, filed on Sep. 15, 2016.

(51) Int. Cl.
*C12P 19/34* (2006.01)
*C12N 15/10* (2006.01)
(Continued)

(52) U.S. Cl.
CPC ...... *C12N 15/1037* (2013.01); *C07K 14/7051* (2013.01); *C07K 16/00* (2013.01);
(Continued)

(58) Field of Classification Search
USPC .......... 435/6.1, 6.11, 6.12, 91.1, 91.2, 283.1, 435/287.1, 287.2; 436/94, 501;
(Continued)

(56) References Cited

U.S. PATENT DOCUMENTS

| 8,143,007 B2 | 3/2012 | Devinder et al. |
| 2002/0012909 A1 | 1/2002 | Plaksin |

(Continued)

FOREIGN PATENT DOCUMENTS

| EP | 1516929 A2 | 3/2005 |
| WO | WO 2010/039852 | 4/2010 |

(Continued)

OTHER PUBLICATIONS

Abi-Ghanem et al., Phage display selection and characterization of single-chain recombinant antibodies against Eimeria . . . , 2008, Vet Immunol Immunopathol vol. 121, pp. 58-67.

(Continued)

*Primary Examiner* — Frank W Lu
(74) *Attorney, Agent, or Firm* — HelixIP LLP

(57) ABSTRACT

The present invention relates generally to the field of immune binding proteins and method for obtaining immune binding proteins from genomic or other sources. The present invention also relates to nucleic acids encoding the immune binding proteins in which the natural multimeric association of chains is maintained in the nucleic acids and the immune binding proteins made therefrom. For example nucleic acids encoding antibodies that are amplified from a B-cell using the methods of the invention maintain the natural pairing of heavy and light chains from the B-cell. This maintenance of pairing (or multimerization) produces libraries and/or repertoires of immune binding proteins that are enriched for useful binding molecules.

6 Claims, 1 Drawing Sheet

(51) Int. Cl.
C07K 14/725 (2006.01)
C07K 16/00 (2006.01)
(52) U.S. Cl.
CPC ..... *C12N 15/1065* (2013.01); *C12N 15/1096* (2013.01); *C07K 2317/10* (2013.01); *C07K 2317/56* (2013.01); *C07K 2317/622* (2013.01)
(58) Field of Classification Search
USPC .......................... 536/23.1, 24.3, 24.33, 25.3
See application file for complete search history.

(56) References Cited

U.S. PATENT DOCUMENTS

| | | |
|---|---|---|
| 2002/0151690 A1 | 10/2002 | Luxemburg |
| 2008/0171329 A1 | 7/2008 | Trnovsky |
| 2012/0252742 A1 | 10/2012 | Kranz et al. |
| 2013/0344508 A1 | 12/2013 | Schwartz et al. |
| 2015/0079581 A1 | 3/2015 | Iwamoto et al. |
| 2016/0032279 A1 | 2/2016 | Daugherty et al. |
| 2016/0060621 A1 | 3/2016 | Agresti et al. |
| 2016/0237489 A1 | 8/2016 | Shen et al. |
| 2016/0252495 A1 | 9/2016 | Ricicova et al. |
| 2016/0312298 A1 | 10/2016 | Ting et al. |
| 2018/0073014 A1 | 3/2018 | Emig et al. |
| 2018/0238775 A1 | 8/2018 | Kambara et al. |
| 2018/0258422 A1 | 9/2018 | Johnson et al. |

FOREIGN PATENT DOCUMENTS

| | | |
|---|---|---|
| WO | WO 2012/034221 | 2/2012 |
| WO | WO 2015/038817 | 3/2015 |
| WO | WO 2016/126871 | 8/2016 |
| WO | WO 2018/013918 | 1/2018 |
| WO | WO 2019/157529 | 8/2019 |

OTHER PUBLICATIONS

Aggen, Engineering Human Single Chain T Cell Receptors, Doctoral Thesis submitted in 2010.

Boria et al., Primer sets for cloning the human repertoire of T cell Receptor Variable regions, 2008, BMC Immunol. vol. 9, p. 50 doi10.1186/1471-2172-9-50.

Cheng et al., Construction and characterization of single-chain variable fragment antibody library derived from germline . . . , 2011, PLoS ONE vol. 6, pp. e27406.

Clontech, A SMARTer approach to T-cell receptor profiling, 2015.

Coronella et al., Amplification of IgG VH and VL (Fab) from single human plasma cells and B cells, 2000, Nucl Acids Res vol. 28, p. e85.

Dekosky et al., High-throughput sequencing of the paired human immunoglobulin heavy and light chain repertoire, 2013, Nat Biotechnol vol. 31, pp. 166-169.

Imai et al., Quality enhancement of the non-immune phage scFv library to isolate effective antibodies, 2006, Biol. Pharm. Bull. vol. 29, pp. 1325-1330.

Kim et al., Analysis of the paired TCR alpha and beta chains of single human T cells, 2012, PLoS ONE vol. 7, pp. e37338.

Pansri et al., A compact phave display human scFv library for selection of antibodies to a wide variety of antigens, BMC Biotechnol vol. 9:6, doi:10.1186/1472-6750-9-6.

Seitz et al., Reconstitution of paired T cell receptor alpha and beta chains from microdissected single cells of human . . . , Proc Natl Acad Sci vol. 103, pp. 12057-12062.

Walchli et al., A practical approach to T-Cell receptor cloning and expression, 2011, PLoS ONE vol. 6, pp. e27930.

Wang et al., Degenerated primer design to amplify the heacy chain variable region from immunoglobulin cDNA, 2006, BMC Bioinform vol. 7(suppl), p. S9.

Bentzen et al., Large-scale detection of antigen specific T cells using peptide-MHC-I multimers labeled with DNA barcodes, 2016, Nat Biotechnol vol. 34, pp. 1037-1045.

Dekosky et al., Large-scale sequence and structural comparisons of human naive and antigen-experienced antibody repertoires, 2016, Proc Nat'l Acad Sci vol. 113, pp. E2636-E2645.

Bigdeli et al, A simple method for encapsulating single cells in alginate microspheres allows for direct PCR and whole genome application, 2015, PLoS ONE vol. 10, pp. 1-15.

Huang et al, Microfluidic generation and manipulation of hydrogel microcapsules for biomimetic 3D tissue culture and . . . , 2016, The Ohio State University, dissertions online, Partial dissertion comprising 100 pages.

Dekosky et al, Large-scale sequence and structural comparisons of human naive and antigen-experienced antibody repertoires, 2016, PNAS vol. 113, pp. E2636-E2645.

Dekosky et al, In-depth determination and analysis of the human paired heavy- and light-chain antibody repertoire, 2015, Nature Med. vol. 21, pp. 86-91.

IMMUNE REPERTOIRE SEQUENCE AMPLIFICATION METHODS AND APPLICATIONS

This application claims priority to provisional application Ser. No. 62/395,241 filed Sep. 15, 2016.

FIELD OF THE INVENTION

The present invention relates generally to the field of immune binding proteins and methods for obtaining immune binding proteins from genomic or other sources. The present invention also relates to nucleic acids encoding the immune binding proteins in which the natural multimeric association of chains is maintained in the nucleic acids and the immune binding proteins made therefrom. For example nucleic acids encoding antibodies that are amplified from a B-cell using the methods of the invention maintain the natural pairing of heavy and light chains from the B-cell. This maintenance of pairing (or multimerization) produces libraries and/or repertoires of immune binding proteins that are enriched for useful binding molecules.

BACKGROUND OF THE INVENTION

There is considerable interest in being able to discover antibodies to specific antigens. Such antibodies are useful as research tools and for diagnostic and therapeutic applications. However, the identification of such useful antibodies is difficult and once identified, these antibodies often require considerable redesign before they are suitable for therapeutic applications in humans.

Many methods for identifying antibodies involve display of antibody libraries derived by amplification of nucleic acids from B cells or other tissues. These approaches have limitations that limit the useful antibodies obtained from the library. For example, most antibody libraries do not pair the heavy and light chains obtained from memory B-cells or plasma cells that have mounted an effective immune response against an immunological challenge. In addition, most human antibody libraries known contain only the antibody sequence diversity that can be experimentally captured or cloned from a biological source (e.g., B cells). Accordingly, such libraries may over-represent some sequences, while completely lacking or under-representing other sequences especially paired light and heavy chains that form useful antibodies, particularly those from a successful immune response.

It is an object of this invention to provide libraries of immune binding proteins that are enriched for useful immune binding proteins. It is also an object of the invention to provide methods for making such libraries that are enriched for useful multimers of immune binding proteins. It is a further object of the invention to provide methods for amplifying nucleic acids from B-cells and plasma cells so that the pairing of light and heavy chains is maintained. It is an object of the invention to obtain libraries of antibodies relevant to disease therapies by obtaining paired light and heavy chain antibodies from individuals whom have mounted antibody responses against a variety of immunologic challenges related to, for example, infectious diseases, cancer, auto-immune disease, neurodegenerative disease, and allergies.

SUMMARY OF THE INVENTION

The invention relates to nucleic acids encoding immune binding proteins that preserve the in vivo multimeric associations of the immune polypeptide chains making up the immune binding protein (e.g., antibodies, T-lymphocyte receptors, or innate immunity receptors). In some embodiments, the invention relates to immune binding protein libraries that are enriched for nucleic acids encoding multimers that functionally represent the multimeric complexes found in the cells from which the immune binding protein library was obtained. In some embodiments, the nucleic acids encoding the polypeptide chains for immune binding proteins are derived from individuals whom have mounted an immune response relevant to, for example, an infectious disease, a cancer, an autoimmune disease, an allergy, or a neurodegenerative disease. In some embodiments, the infectious disease is caused by an influenza virus. In some embodiments, the infectious disease is caused by a virus such as, for example, HIV, Ebola, Zika, HSV, RSV, or CMV. In some embodiments, the cancer is a melanoma. In some embodiments, the cancer is one that responds to immunotherapy.

The invention relates to nucleic acids encoding polypeptide chains for immune binding proteins of the invention (e.g., light and heavy chain antibody polypeptides) that preserve the in vivo functional pairing of the polypeptide chains (e.g., light and heavy chains of an antibody). In some embodiments, the immune binding protein libraries of the invention are enriched for functional multimers of nucleic acids encoding the polypeptide chains that make up the immune binding protein (e.g., light and heavy chains of an antibody) and which were associated together in the repertoire from which the immune binding protein library was obtained. In some embodiments, the nucleic acids encoding associated polypeptide chains for the immune binding protein (e.g., paired light and heavy chains) are derived from individuals whom have mounted an immune response relevant to, for example, an infectious disease, a cancer, an autoimmune disease, an allergy, or a neurodegenerative disease. In some embodiments, the infectious disease is caused by an influenza virus. In some embodiments, the infectious disease is caused by a virus such as, for example, HIV, Ebola, Zika, HSV, RSV, or CMV.

In some embodiments, the invention relates to a plurality of nucleic acids comprising a plurality of polynucleotides encoding a first chain of a multimeric immune binding protein, a plurality of polynucleotides encoding a second chain of a multimeric immune binding protein, wherein each polynucleotide encoding the first chain of the multimeric immune binding protein is paired with the polynucleotide encoding the second chain of the immune binding protein to form a plurality of pairs of polynucleotides encoding the first chain and the second chain, wherein the plurality of pairs of polynucleotides represent a plurality of pairs of first chains and second chains as they are found in a plurality of host cells from which the multimeric immune binding proteins are derived. In some embodiments, the multimeric immune binding protein is an antibody, a T-cell receptor or an innate immunity receptor. In some embodiments, the antibody is a scFv, a Fab, a F(ab')$_2$, a Fab', a Fv, or a diabody. In some embodiments, the antibody is an IgG, an IgM, an IgA, an IgD, or an IgE. In some embodiments, the antibody is from a B-cell, a plasma cell, a B memory cell, a pre-B-cell or a progenitor B-cell. In some embodiments, the T-cell receptor is a single chain T-cell receptor. In some embodiments, the T-cell receptor is from a CD8+ T-cell, a CD4+ T-cell, a regulatory T-cell, a memory T-cell, a helper T-cell, or a cytotoxic T-cell. In some embodiments, the multimeric immune binding protein is from a natural killer cell, a macrophage, a monocyte, or a dendritic cell.

In some embodiments, individual cells containing nucleic acids encoding the immune binding proteins are placed into microwells and/or an emulsion. In some embodiments, primers for the forward (F) and reverse (R) directions of the nucleic acids encoding the polypeptides for the immune binding protein (e.g., antibody heavy (H) and light (L) chains) are introduced (e.g., HF, HR, LF, and LR), as well as a polymerase enzyme and dNTPs to carry out template-directed amplification. In some embodiments, the F1 (e.g., HF) and R2 (e.g., LR) primers (or alternatively the LF and HR primers) contain an overlap extension region (OE) such that during cycled amplification these primers mutually extend each other. In some embodiments, a joint polypeptide (such as a scFv) can be encoded by the amplified nucleic acids, the OE region can also encode an amino acid linker sequence (FIG. 1A). In an alternate embodiment, the amplified nucleic acids are used in a sequencing reaction and one or more of the primers can include a barcode region (e.g., BC1, BC2, BC3 and/or BC4) (FIG. 1B). In some embodiments, the amplification reaction is carried out, resulting in a nucleic acid which codes for the two polypeptide chains of the immune binding protein (e.g., both a heavy and a light chain of an antibody). In some embodiments, the nucleic acid obtained from each well and/or emulsion is homogeneous and encodes the antibody made by the single cell placed in the microwell and/or emulsion. In some embodiments, nucleic acids obtained from the wells and/or emulsions are pooled to form a library of immune binding proteins (e.g., heavy/light chain pairs) that reflect the association of polypeptides (e.g., pairing of the antibody chains) from the source cells or genetic material.

In some embodiments, the resulting pool of nucleic acids encoding associated polypeptides of the immune binding protein (e.g., paired heavy and light chains for and antibody) are cloned into an expression vector or can be processed for sequencing. In some embodiments, the expression vector is engineered for phage display, yeast display, or other display technology. In some embodiments, the expression vector is for secretion expression and recombinant production of the immune binding protein. In some embodiments, the expression vector is for making a library of chimeric antigen receptors, where each CAR has one of the associated immune binding protein clones obtained from the amplification reaction. In some embodiments, primers corresponding to heavy chains or light chains may be targeted to single isotypes of antibodies (e.g., IgG), or pools of primers corresponding to all available isotypes or some fraction thereof may be used.

In some embodiments, primers for the polypeptide chains of the immune binding protein (e.g., light chain and heavy chains of an antibody) are linked together so that each primer is capable of priming a reaction. In some embodiments, a 5' azide-alkyne reaction ("Click") coupling can bring together the primers. In this embodiment, the dual primer is incubated with single cells in a well or emulsion, and nucleic acids are obtained where a nucleic acid encoding one polypeptide chain of the immune binding protein is linked to a nucleic acid encoding the associated polypeptide chain of the same immune binding protein (e.g., a heavy chain is linked to a nucleic acid encoding the paired light chain). In some embodiments, a microsurface (e.g., bead or microwell) is prepared and contains primer sequences that are capable of binding nucleic acids encoding multiple, associated polypeptides of the immune binding protein (e.g., heavy and light chain nucleic acids). Following mRNA capture, cDNA synthesis or PCR from a single cell in a spatial confinement with the primers in the well or on the bead, nucleic acids encoding the associated polypeptide chains (e.g., paired heavy and light chains) become co-located with the primers of the solid phase.

In some embodiments, nucleic acid probes for nucleic acids encoding associated polypeptides of the immune binding protein (e.g., heavy and light chain polypeptides) are placed on a solid surface. In this embodiment, the probes for nucleic acids encoding associated polypeptides of the immune binding protein (e.g., heavy and light chain polypeptides) are interrogated with nucleic acids, e.g., mRNA, from a single cell. The probes on the solid phase will capture nucleic acids encoding the associated polypeptides of the immune binding protein (e.g., heavy and light chain polypeptides) from the cell. In some embodiments, captured mRNA is reverse transcribed to make paired cDNAs encoding associated polypeptides of the immune binding protein (e.g., heavy and light chain polypeptides) from a single cell.

In some embodiments, the nucleic acids encoding the subunits of the immune binding protein are bar coded to enable identification of unique molecules. In some embodiments, a solid phase with a cell-specific barcode is made with spatially confined PCR reactions of a plurality of single template molecules containing a linker/adapter primer sequence, a random barcode sequence, and a secondary primer sequence. In some embodiments, a limited dilution of template molecules is used, and the template molecule is linked to a solid phase at very low loading rates to ensure only a single molecule is available as a template at each site. In this embodiment, at least one of the primers in this PCR reaction should be attached to the solid phase. In some embodiments, additional molecules may be added to load additional sites, knowing that previously bound sites are incapable of reacting because they were exhausted during previous rounds of PCR. In some embodiments, oligonucleotides can be attached at an extremely low loading rate to a surface and beads are flowed over the surface to ensure that each bead binds a single oligonucleotide. In some embodiments, beads are reflowed over the surface without being subjected to the constraints of poissonian loading. In some embodiments, each bound bead would be guaranteed to have one and only one template sequence. In some embodiments, each spatially confined site (either a position or well on a patterned surface, or bead in emulsion) will contain the same barcoded DNA in close proximity, whereas other sites will each contain separate barcoded DNA in close proximity originating from other single molecule templates. In some embodiments, single stranded DNA can be generated through the use of a 5' nuclease or denaturation of the uncoupled second strand. In this embodiment, the secondary primer sequence is available to perform a subsequent barcode extension reaction, or can be used directly to capture nucleic acids from single cells. In some embodiments, the bead can be ligated to a sequence containing a linker section and a fully random sequence to serve as a unique molecular identifier, and a tertiary primer sequence. In this embodiment, the tertiary primer sequence is available to perform a subsequent barcode extension reaction, or can be used directly to capture nucleic acids from single cells.

In some embodiments, the antigens are identified for the immune binding proteins of the invention. In some embodiments, the nucleic acids of the invention encode the subunits (or pairs) of the immune binding protein and the antigen bound by the immune binding protein. In some embodiments, a three-way coupling between nucleic acids encoding associated polypeptides of the immune binding protein (e.g., heavy and light chain polypeptides), and an antigen that is barcoded with an antigen-specific sequence. In some embodiments, antibodies are displayed on the surface of a cell, probed with a population of barcoded antigens, and then the resulting conjugates can be encapsulated into a microwell or an emulsion, and sequence amplification methods are utilized to recover the sequence of the associated polypeptides of the immune binding protein (e.g., heavy and light chain polypeptides) and the barcoded antigen sequence. In some embodiments, a plurality of antigens are bar coded. The bar coded antigens can screened against immune binding proteins to find the immune binding proteins that bind to specific antigens. This screening can be done with immune binding proteins from the libraries described herein, immune cells obtained from a subject who is naïve to the antigen, or immune cells obtained from a subject who has mounted a relevant immune response (e.g., an immune response relevant to an infectious disease, a cancer, an autoimmune disease, an allergy, or a neurodegenerative disease). The immune cells paired with bar coded antigens can then be used in the amplification methods to obtain nucleic acids encoding immune binding proteins and the immune binding proteins.

In some embodiments, the nucleic acids encoding the immune binding proteins are sequenced. In some embodiments, the sequencing is done by high-throughput sequencing. In some embodiments, the sequence information obtained is used for putative lineage information based on sequence alignment.

BRIEF DESCRIPTION OF THE FIGURES

FIG. 1A shows a reaction using light chain forward (LF) and light chain reverse (LR) primers where the LR primer includes an overlap extension region (OE). FIG. 1A also shows heavy chain forward (HF) and heavy chain reverse (HR) primers where the HF primer also includes an overlap extension region (OE). FIG. 1B shows an embodiment where one or more of the primers include a bar code region for identification of the nucleic acid made by the primers. FIG. 1C shows an embodiment where an antigen includes a nucleic acid that identifies the antigen, and which nucleic acid also has forward and reverse primers (antigen forward AF and antigen reverse AR) where the AR primer has an overlap region that will correspond to an overlap region of one of the heavy chain or light chain primers, e.g., the LF primer can include an OE that will correspond to the OE of the AR primer.

DETAILED DESCRIPTION OF THE INVENTION

Figure 1A:
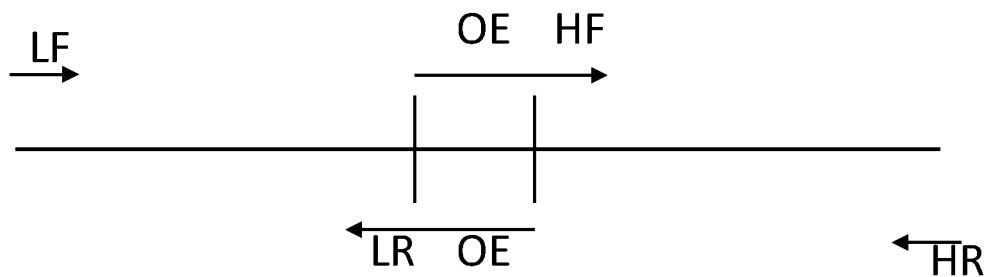
FIG. 1A-C show depictions of primers used in the invention and nucleic acid products made by the invention.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

It must be noted that as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation. Numerical limitations given with respect to concentrations or levels of a substance are intended to be approximate, unless the context clearly dictates otherwise. Thus, where a concentration is indicated to be (for example) 10 µg, it is intended that the concentration be understood to be at least approximately or about 10 µg.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Definitions

As used herein, an "antibody" refers to a protein functionally defined as a binding protein and structurally defined as comprising an amino acid sequence that is recognized as being derived from the framework region of an immunoglobulin encoding gene of an animal producing antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well-characterized fragments. Thus, for example, pepsin digests an antibody below the disulfide linkages in the hinge region to produce F(ab)'$_2$, a dimer of Fab which itself is a light chain joined to VH-CH1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody, as used herein also includes antibody fragments either produced by the modification of whole antibodies or synthesized using recombinant DNA methodologies. Preferred antibodies include $V_H$-$V_L$ dimers, including single chain antibodies (antibodies that exist as a single polypeptide chain), such as single chain Fv antibodies (sFv or scFv) in which a variable heavy and a variable light region are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker (e.g., Huston, et al. Proc. Nat. Acad. Sci. USA, 85:5879-5883, 1988). While the $V_H$ and $V_L$ are connected to each as a single polypeptide chain, the $V_H$ and $V_L$ domains associate non-covalently. Alternatively, the antibody can be another fragment. Other fragments can also be generated, including using recombinant techniques. For example Fab molecules can be displayed on phage if one of the chains (heavy or light) is fused to g3 capsid protein and the complementary chain exported to the periplasm as a soluble molecule. The two chains can be encoded on the same or on different replicons; the two antibody chains in each Fab molecule assemble post-translationally and the dimer is incorporated into the phage particle via linkage of one of the chains to g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). In some embodiments, the scFv is a diabody as described in Holliger et al., Proc. Nat'l Acad. Sci. vol. 90, pp. 6444-6448 (1993), which is incorporated by reference in its entirety for all purposes. In some embodiments, antibodies include all those that have been displayed on phage or generated by recombinant technology using vectors where the chains are secreted as soluble proteins, e.g., scFv, Fv, Fab, pr (Fab')$_2$ or generated by recombinant technology using vectors where the chains are secreted as soluble proteins. Antibodies can also include diantibodies and miniantibodies.

Antibodies of the invention also include heavy chain dimers, such as antibodies from camelids. Since the $V_H$ region of a heavy chain dimer IgG in a camelid does not have to make hydrophobic interactions with a light chain, the region in the heavy chain that normally contacts a light chain is changed to hydrophilic amino acid residues in a camelid. $V_H$ domains of heavy-chain dimer IgGs are called $V_{HH}$ domains.

In camelids, the diversity of antibody repertoire is determined by the complementary determining regions (CDR) 1, 2, and 3 in the $V_H$ or $V_{HH}$ regions. The CDR3 in the camel $V_{HH}$ region is characterized by its relatively long length averaging 16 amino acids (Muyldermans et al., 1994, Protein Engineering 7 (9): 1129). This is in contrast to CDR3 regions of antibodies of many other species. For example, the CDR3 of mouse $V_H$ has an average of 9 amino acids.

Libraries of camelid-derived antibody variable regions, which maintain the in vivo diversity of the variable regions of a camelid, can be made by, for example, the methods disclosed in U.S. Patent Application Ser. No. 20050037421, published Feb. 17, 2005.

As used herein, the term "naturally occurring" means that the components are encoded by a single gene that was not altered by recombinant means and that pre-exists in an organism, e.g., in an antibody library that was created from naive cells or cells that were exposed to an antigen.

As used herein, the term "antigen" refers to substances that are capable, under appropriate conditions, of inducing a specific immune response and of reacting with the products of that response, such as, with specific antibodies or specifically sensitized T-lymphocytes, or both. Antigens may be soluble substances, such as toxins and foreign proteins, or particulates, such as bacteria and tissue cells; however, only the portion of the protein or polysaccharide molecule known as the antigenic determinant (epitopes) combines with the antibody or a specific receptor on a lymphocyte. More broadly, the term "antigen" may be used to refer to any substance to which an antibody binds, or for which antibodies are desired, regardless of whether the substance is immunogenic. For such antigens, antibodies may be identified by recombinant methods, independently of any immune response.

As used herein, the term "epitope" refers to the site on an antigen or hapten to which specific B cells and/or T cells respond. The term is also used interchangeably with "antigenic determinant" or "antigenic determinant site". Epitopes include that portion of an antigen or other macromolecule capable of forming a binding interaction that interacts with the variable region binding pocket of an antibody.

As used herein, the term "binding specificity" of an antibody refers to the identity of the antigen to which the antibody binds, preferably to the identity of the epitope to which the antibody binds.

As used herein, the term "chimeric polynucleotide" means that the polynucleotide comprises regions which are wild-type and regions which are mutated. It may also mean that the polynucleotide comprises wild-type regions from one polynucleotide and wild-type regions from another related polynucleotide.

As used herein, the term "complementarity-determining region" or "CDR" refer to the art-recognized term as exemplified by the Kabat and Chothia. CDRs are also generally known as hypervariable regions or hypervariable loops (Chothia and Lesk (1987) J Mol. Biol. 196: 901; Chothia et al. (1989) Nature 342: 877; E. A. Kabat et al., Sequences of Proteins of Immunological Interest (National Institutes of Health, Bethesda, Md.) (1987); and Tramontano et al. (1990) J Mol. Biol. 215: 175). "Framework region" or "FR" refers to the region of the V domain that flank the CDRs. The positions of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. J. Mol. Biol. 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., J. Mol. Biol 1997, 273(4)). Definitions of antigen combining sites are also described in the following: Ruiz et al., IMGT, the international ImMunoGeneTics database. Nucleic Acids Res., 28, 219-221 (2000); and Lefranc, M.-P. IMGT, the international ImMunoGeneTics database. Nucleic Acids Res. January 1; 29 (1):207-9 (2001); MacCallum et al, Antibody-antigen interactions: Contact analysis and binding site topography, J. Mol. Biol., 262 (5), 732-745 (1996); and Martin et al, Proc. Natl Acad. Sci. USA, 86, 9268-9272 (1989); Martin, et al, Methods Enzymol., 203, 121-153, (1991); Pedersen et al, Immunomethods, 1, 126, (1992); and Rees et al, In Sternberg M. J. E. (ed.), Protein Structure Prediction. Oxford University Press, Oxford, 141-172 1996).

As used herein, the term "hapten" is a small molecule that, when attached to a larger carrier such as a protein, can elicit an immune response in an organism, e.g., such as the production of antibodies that bind specifically to it (in either the free or combined state). A "hapten" is able to bind to a preformed antibody, but may fail to stimulate antibody generation on its own. In the context of this invention, the term "hapten" includes modified amino acids, either naturally occurring or non-naturally occurring. Thus, for example, the term "hapten" includes naturally occurring modified amino acids such as phosphotyrosine, phosphothreonine, phosphoserine, or sulphated residues such as sulphated tyrosine (sulphotyrosine), sulphated serine (sulphoserine), or sulphated threonine (sulphothreonine); and also include non-naturally occurring modified amino acids such as p-nitro-phenylalanine.

As used herein, the term "heterologous" when used with reference to portions of a polynucleotide indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid. Similarly, a "heterologous" polypeptide or protein refers to two or more subsequences that are not found in the same relationship to each other in nature.

As used herein, the term "host cell" refers to a prokaryotic or eukaryotic cell into which the vectors of the invention may be introduced, expressed and/or propagated. A microbial host cell is a cell of a prokaryotic or eukaryotic micro-organism, including bacteria, yeasts, microscopic fungi and microscopic phases in the life-cycle of fungi and slime molds. Typical prokaryotic host cells include various strains of *E. coli*. Typical eukaryotic host cells are yeast or filamentous fungi, or mammalian cells, such as Chinese hamster ovary cells, murine NIH 3T3 fibroblasts, human embryonic kidney 193 cells, or rodent myeloma or hybridoma cells.

As used herein, the term "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

As used herein, the term "isolated" refers to a nucleic acid or polypeptide separated not only from other nucleic acids or polypeptides that are present in the natural source of the nucleic acid or polypeptide, but also from polypeptides, and preferably refers to a nucleic acid or polypeptide found in the presence of (if anything) only a solvent, buffer, ion, or other component normally present in a solution of the same. The terms "isolated" and "purified" do not encompass nucleic acids or polypeptides present in their natural source.

As used herein, the term "mammal" refers to warm-blooded vertebrate animals all of which possess hair and suckle their young.

As used herein, "percentage of sequence identity" and "percentage homology" are used interchangeably herein to refer to comparisons among polynucleotides or polypeptides, and are determined by comparing two optimally aligned sequences over a comparison window, where the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, *Adv Appl Math.* 2:482, 1981; by the homology alignment algorithm of Needleman and Wunsch, *J Mol Biol.* 48:443, 1970; by the search for similarity method of Pearson and Lipman, *Proc Natl Acad Sci. USA* 85:2444, 1988; by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Greene Publishing Associates, Inc. and John Wiley & Sons, Inc., (1995 Supplement). Examples of algorithms that are suitable for determining percent sequence identity and sequence similarity are the BLAST and BLAST 2.0 algorithms, which are described in Altschul et al., *J. Mol. Biol.* 215:403-410, 1990; and Altschul et al.,*Nucleic Acids Res.* 25 (17):3389-3402, 1977; respectively. Software for performing BLAST analyses is publicly available through the National Center for Biotechnology Information website. BLAST for nucleotide sequences can use the BLASTN program with default parameters, e.g., a wordlength (W) of 11, an expectation (E) of 10, M=5, N=-4, and a comparison of both strands. BLAST for amino acid sequences can use the BLASTP program with default parameters, e.g., a wordlength (W) of 3, an expectation (E) of 10, and the BLOSUM62 scoring matrix (see Henikoff and Henikoff, *Proc Natl Acad Sci. USA* 89:10915, 1989). Exemplary determination of sequence alignment and % sequence identity can also employ the BESTFIT or GAP programs in the GCG Wisconsin Software package (Accelrys, Madison Wis.), using default parameters provided.

As used herein, the terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the term "purified" means that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99.8% by weight, of the indicated biological macromolecules present (but water, buffers, and other small molecules, especially molecules having a molecular weight of less than 1000 daltons, can be present)

As used herein, the term "recombinant nucleic acid" refers to a nucleic acid in a form not normally found in nature. That is, a recombinant nucleic acid is flanked by a nucleotide sequence not naturally flanking the nucleic acid or has a sequence not normally found in nature. Recombinant nucleic acids can be originally formed in vitro by the manipulation of nucleic acid by restriction endonucleases, or alternatively using such techniques as polymerase chain reaction. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention.

As used herein, the term "recombinant polypeptide" refers to a polypeptide expressed from a recombinant nucleic acid, or a polypeptide that is chemically synthesized in vitro.

As used herein, the term "recombinant variant" refers to any polypeptide differing from naturally occurring polypeptides by amino acid insertions, deletions, and substitutions, created using recombinant DNA techniques. Guidance in determining which amino acid residues may be replaced, added, or deleted without abolishing activities of interest, such as enzymatic or binding activities, may be found by comparing the sequence of the particular polypeptide with that of homologous peptides and minimizing the number of amino acid sequence changes made in regions of high homology.

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

As used herein, the terms "repertoire" or ""library" refers to a library of genes encoding antibodies or antibody fragments such as Fab, scFv, Fd, LC, $V_H$, or $V_L$, or a subfragment of a variable region, e.g., an exchange cassette, that is obtained from a natural ensemble, or "repertoire", of antibody genes present, e.g., in human donors, and obtained primarily from the cells of peripheral blood and spleen. In some embodiments, the human donors are "non-immune", i.e., not presenting with symptoms of infection. In the current invention, a library or repertoire often comprises members that are exchange cassette of a given portion of a V region.

As used herein, the term "synthetic antibody library" refers to a library of genes encoding one or more antibodies or antibody fragments such as Fab, scFv, Fd, LC, $V_H$, or $V_L$, or a subfragment of a variable region, e.g., an exchange cassette, in which one or more of the complementarity-determining regions (CDR) has been partially or fully altered, e.g., by oligonucleotide-directed mutagenesis. "Randomized" means that part or all of the sequence encoding the CDR has been replaced by sequence randomly encoding all twenty amino acids or some subset of the amino acids.

As used herein, a T-cell" is defined to be a hematopoietic cell that normally develops in the thymus. T-cells include, but are not limited to, natural killer T cells, regulatory T cells, helper T cells, cytotoxic T cells, memory T cells, gamma delta T cells and mucosal invariant T cells. T-cells also include, but are not limited to CD8+ T-cells, CD4+ T-cells, Th1 T-cells, and Th2 T-cells.

The singular terms "a", "an", and "the" include plural referents unless context clearly indicates otherwise. Similarly, the word "or" is intended to include "and" unless the context clearly indicates otherwise. Numerical limitations given with respect to concentrations or levels of a substance, such as an antigen, are intended to be approximate. Thus, where a concentration is indicated to be at least (for example) 200 it is intended that the concentration be understood to be at least approximately "about" or "about" 200 µg.

Immune Binding Proteins

In some embodiments, the immune binding protein is an antibody, a T-cell receptor, or an innate immunity receptor. In some embodiments, the immune binding protein is from a cell of the immune system including, for example, a B-cell, a plasma cell, a T-cell, a natural killer cell, a dendritic cell, or a macrophage.

In some embodiments, antibodies are immune binding proteins that are structurally defined as comprising an amino acid sequence recognized as being derived from the framework region of an immunoglobulin. In some embodiments, an antibody consists of one or more polypeptides substantially encoded by immunoglobulin genes or fragments of immunoglobulin genes. In some embodiments, the immunoglobulin genes include, for example, the kappa, lambda, alpha, gamma, delta, epsilon and mu constant region genes, as well as myriad immunoglobulin variable region genes. In some embodiments, antibody light chains are classified as either kappa or lambda. In some embodiments, antibody heavy chains are classified as gamma, mu, alpha, delta, or epsilon, which in turn define the immunoglobulin classes, IgG, IgM, IgA, IgD and IgE, respectively.

In some embodiments, antibodies exist as intact immunoglobulins or as a number of well-known fragments. In some embodiments, pepsin digests an antibody below the disulfide linkages in the hinge region to produce $F(ab)'_2$, a dimer of Fab which itself is a light chain joined to VH-CH1 by a disulfide bond. In some embodiments, the $F(ab)'_2$ may be reduced under mild conditions to break the disulfide linkage in the hinge region thereby converting the $(Fab')_2$ dimer into Fab' monomers. In some embodiments, the Fab' monomer is an Fab with part of the hinge region (see, Fundamental Immunology, W. E. Paul, ed., Raven Press, N.Y. (1993), which is incorporated by reference in its entirety for all purposes). In some embodiments, antibody fragments are synthesized de novo either chemically or by utilizing recombinant DNA methodology. In some embodiments, antibodies include $V_H$-$V_L$ dimers, including single chain antibodies (antibodies that exist as a single polypeptide chain), such as diabodies, or single chain Fv antibodies (sFv or scFv) in which a variable heavy and a variable light region are joined together (directly or through a peptide linker) to form a continuous polypeptide. (e.g., Huston, et al. Proc. Nat. Acad. Sci. USA, 85:5879-5883, 1988, which is incorporated by reference in its entirety for all purposes). In some embodiments, antibodies can be another fragment, including, for example, Fab molecules displayed on phage if one of the chains (heavy or light) is fused to g3 capsid protein and the complementary chain exported to the periplasm as a soluble molecule. (e.g., U.S. Pat. No. 5,733,743, which is incorporated by reference in its entirety for all purposes). In some embodiments, the antibody is an scFv antibody or a number of other structures converting the naturally aggregated, but chemically separated light and heavy polypeptide chains from an antibody V region into a molecule that folds into a three dimensional structure substantially similar to the structure of an antigen-binding site are known to those of skill in the art (e.g., U.S. Pat. Nos. 5,091,513, 5,132,405, and 4,956,778, which are all incorporated by reference in their entirety for all purposes). In some embodiments, the scFv is a diabody as described in Holliger et al., Proc. Nat'l Acad. Sci. vol. 90, pp. 6444-6448 (1993), which is incorporated by reference in its entirety for all purposes. In some embodiments, antibodies include all those that have been displayed on phage or generated by recombinant technology using vectors where the chains are secreted as soluble proteins, e.g., scFv, Fv, Fab, pr (Fab')$_2$. Antibodies can also include miniantibodies. In some embodiments, the antibody is from a B-cell, a plasma cell, a B memory cell, a pre-B-cell or a progenitor B-cell.

In some embodiments, the immune binding protein is a T-cell receptor. In some embodiments, the T-cell receptor is from a CD8+ T-cell, a CD4+ T-cell, a regulatory T-cell, a memory T-cell, a helper T-cell, or a cytotoxic T-cell. In some embodiments, T-cell receptors are obtained from either (or both) the genomic DNA of the T-cells (or subpopulation of T-cells) and/or the mRNA of the T-cells (or subpopulation of T-cells). In some embodiments, repertoires of T-cell receptors are obtained using techniques and primers well known in the art and described in, for example, SMARTer Human TCR a/b Profiling Kits sold commercially by Clontech, Boria et al., BMC Immunol. 9:50-58 (2008); Moonka et al., J. Immunol. Methods 169:41-51 (1994); Kim et al., PLoS ONE 7:e37338 (2012); Seitz et al., Proc. Natl Acad. Sci. 103:12057-62 (2006), all of which are incorporated by reference in their entirety for all purposes. In some embodiments, the T-cell receptors are used as separate chains to form an immune binding protein. In some embodiments, the T-cell receptors are converted to single chain antigen binding domains. In some embodiments, single chain T-cell receptors are made from nucleic acids encoding human alpha and beta chains using techniques well-known in the art including, for example, those described in U.S. Patent Application Publication No. US2012/0252742, Schodin et al., Mol. Immunol. 33:819-829 (1996); Aggen et al., "Engineering Human Single-Chain T Cell Receptors," Ph.D. Thesis with the University of Illinois at Urbana-Champaign (2010) a copy of which is found at ideals.illinois.edu/bitstream/handle/2142/18585/aggen_David.pdf?sequence=1, all of which are incorporated by reference in their entirety for all purposes.

In some embodiments, the immune binding protein is an innate immunity receptor. In some embodiments, natural killer cells, dendritic cells, macrophages, T-cells, and/or B-cells are used to make a NKG receptor binding proteins and/or Toll-like receptor binding proteins. In some embodiments, the natural killer cells, dendritic cells, macrophages, T-cells, and/or B-cells are obtained from a subject who has become immune to a disease or has had an immune response to a disease or condition. In some embodiments, the immune binding proteins is obtained from the CD94/NKG2 receptor family (e.g., NKG2A, NKG2B, NKG2C, NKG2D, NKG2E, NKG2F, NKG2H), the 2B4 receptor, the NKp30, NKp44, NKp46, and NKp80 receptors, the Toll-like receptors (e.g., TLR1, TLR2, TLR3, TLR4, TLR5, TLR6, TLR7, TLR8, TLR9, TLR10, RP105), and/or innate immunity receptors are obtained from the subjects immune cells (natural killer cells, dendritic cells, macrophages, T-cells, and B-cells). In some embodiments, the immune binding proteins of the invention are made as described in U.S. Pat. Nos. 5,359,046, 5,686,281 and 6,103,521 (which are hereby incorporated by reference in their entirety for all purposes). In some embodiments, the immune binding protein is part of a receptor which is monomeric, homodimeric, heterodimeric, or associated with a larger number of proteins in a non-covalent complex. In some embodiments, a multimeric receptor has only one polypeptide chain with a major role in binding to the ligand. In these embodiments, the immune binding protein can be derived from the polypeptide chain that binds the ligand. In some embodiments, the immune binding protein is a complex of extracellular portions from several proteins that forms covalent bonds through disulfide linkages. In some embodiments, the immune binding protein is comprised of truncated portions of a receptor, where such truncated portion is functional for binding ligand.

Methods for Amplifying Nucleic Acids Encoding Multimeric Immune Proteins

The invention relates to methods for making nucleic acids encoding immune binding proteins that preserve the in vivo multimeric associations of the immune polypeptide chains making up the immune binding protein (e.g., antibodies, T-lymphocyte receptors or innate immunity receptors). In some embodiments, immune binding protein libraries of the invention are enriched for nucleic acids encoding multimers that are functional polypeptides representing the multimeric complexes found in the repertoire from which the immune binding protein library was obtained. In some embodiments, the nucleic acids encoding the polypeptide chains for immune binding proteins are derived from individuals whom have mounted an immune response relevant to, for example, an infectious disease, a cancer, an autoimmune disease, an allergy, or a neurodegenerative disease. In some embodiments, the infectious disease is caused by an influenza virus. In some embodiments, the infectious disease is caused by a virus such as, for example, HIV, Ebola, Zika, HSV, RSV, or CMV.

In some embodiments, the immune binding proteins are antibodies or are immune binding proteins derived from antibodies. In some embodiments, the immune binding proteins are T-cell receptors from, for example, cytotoxic T-cells, helper T-cells, and memory T-cells. In some embodiments, the immune binding proteins are innate immune receptors such as, for example the CD94/NKG2 receptor family (e.g., NKG2A, NKG2B, NKG2C, NKG2D, NKG2E, NKG2F, NKG2H), the 2B4 receptor, the NKp30, NKp44, NKp46, and NKp80 receptors, the Toll-like receptors (e.g., TLR1, TLR2, TLR3, TLR4, TLR5, TLR6, TLR7, TLR8, TLR9, TLR10, RP105).

In some embodiments, immune binding proteins are made from individual cells that are placed into microwells and/or an emulsion. In some embodiments, forward (F) and reverse (R) primers are used for each individual chain of the immune binding protein (e.g., heavy (H) and light (L) chain primers designated HF, HR, LF, and LR), as well as a polymerase enzyme and dNTPs to carry out template-directed amplification. In some embodiments, the primers for an individual chain of the immune binding protein (e.g., the HF and HL primers for an antibody heavy chain and/or alternatively the LF and HR primers for the antibody light chain) contain an overlap extension region (OE) such that during cycled amplification the primers for one chain extend (amplify) nucleic acids encoding the other chains of the immune binding protein. In some embodiments, a joint polypeptide (such as a scFv or a single chain T-cell receptor) can be encoded by the amplified nucleic acids, and the OE region can optionally encode an amino acid linker sequence.

In some embodiments, the amplification reaction is carried out, resulting in a nucleic acid which codes for each of the polypeptides from the immune binding protein (e.g., both a heavy and a light chain of an antibody). In some embodiments, the nucleic acid obtained from each well and/or emulsion is homogeneous and encodes the immune binding protein (e.g., antibody) made by the single cell placed in the microwell and/or emulsion. In some embodiments, nucleic acids obtained from the wells and/or emulsions are pooled to form a library of heavy/light chain pairs that reflect the pairing of the antibody chains from the source cells or genetic material.

In some embodiments, the resulting pool of nucleic acids encoding paired heavy and light chains for the antibodies are cloned into an expression vector or can be processed for sequencing. In some embodiments, the expression vector is engineered for phage display, yeast display, or other display technology. In some embodiments, the expression vector is for secretion expression and recombinant production of the antibodies. In some embodiments, the expression vector is for making a library of chimeric antigen receptors, where each CAR has one of the paired antibody clones obtained from the amplification reaction. In some embodiments, primers corresponding to heavy chains or light chains may be targeted to single isotypes of antibodies (e.g., IgG), or pools of primers corresponding to all available isotypes or some fraction thereof may be used.

In some embodiments, primers for the light chain and heavy chain are linked together so that each primer is capable of priming a reaction. In some embodiments, a 5' azide-alkyne reaction ("Click") coupling can bring together the heavy and light chain primers. In this embodiment, the dual primer is incubated with single cells in a well or emulsion, and nucleic acids are obtained where a nucleic acid encoding a heavy chain is linked to a nucleic acid encoding the paired light chain. In some embodiments, a microsurface (e.g., bead or microwell) is prepared and contains primer sequences that are capable of binding either heavy or light chain nucleic acids. Following mRNA capture, cDNA synthesis or PCR from a single cell in a spatial confinement with the primers in the well or on the bead, nucleic acids encoding the paired heavy and light chains become co-located with the heavy and light chain primers of the solid phase.

In some embodiments, nucleic acid probes for nucleic acids encoding heavy and light chain polypeptides are placed on a solid surface. In this embodiment, the probes for nucleic acids encoding heavy and light chain antibody polypeptides are interrogated with nucleic acids, e.g., mRNA, from a single cell. The probes on the solid phase will capture paired light and heavy chains encoding nucleic acids from the cell. In some embodiments, captured mRNA is reverse transcribed to make paired cDNAs encoding the light chain and heavy chain polypeptides from a single cell.

In some embodiments, the nucleic acids encoding the subunits of the immune binding protein are bar coded to enable identification of unique molecules. In some embodiments, a solid phase with a cell-specific barcode is made with spatially confined PCR reactions of a plurality of single template molecules containing a linker/adapter primer sequence, a random barcode sequence, and a secondary primer sequence. In some embodiments, a limited dilution of template molecules is used, and the template molecule is linked to a solid phase at very low loading rates to ensure only a single molecule is available as a template at each site. In this embodiment, at least one of the primers in this PCR reaction should be attached to the solid phase. In some embodiments, additional molecules may be added to load additional sites, knowing that previously bound sites are incapable of reacting because they were exhausted during previous rounds of PCR.

In some embodiments, oligonucleotides can be attached at an extremely low loading rate to a surface and beads are flowed over the surface to ensure that each bead binds a single oligonucleotide. In some embodiments, beads are reflowed over the surface without being subjected to the constraints of poissonian loading. In some embodiments, a moderate surface of 100 $cm^2$, hundreds of millions of beads can be bound to individual molecules. In some embodiments, each bound bead would be guaranteed to have one and only one template sequence. In some embodiments, each spatially confined site (either a position or well on a patterned surface, or bead in emulsion) will contain the same barcoded DNA in close proximity, whereas other sites will each contain separate barcoded DNA in close proximity originating from other single molecule templates. In some embodiments, single stranded DNA can be generated through the use of a 5' nuclease or denaturation of the uncoupled second strand. In this embodiment, the secondary primer sequence is available to perform a subsequent barcode extension reaction, or can be used directly to capture nucleic acids from single cells. In some embodiments, the bead can be ligated to a sequence containing a linker section and a fully random sequence to serve as a unique molecular identifier, and a tertiary primer sequence. In this embodiment, the tertiary primer sequence is available to perform a subsequent barcode extension reaction, or can be used directly to capture nucleic acids from single cells.

In some embodiments, a surface (e.g., glass surface) is selectively silanized and functional alkane or PEG (eg FSL, amino, azide, DBCO, fibrous group) is attached in an array of spots that are smaller than the size of the bead or diameter of the cells to be captured. In some embodiments, the remaining surface is silanized with passivating silane (e.g., alkane or PEG). Functional sites may be additionally modified with proteins or moieties to capture desired cells or specific types of cells. For example, CD19 can be attached to the surface for the capture of B cells from a cell mixture. Target cells are incubated with the surface at concentrations where a small number of cells are captured at each site. The cells are then non-poissonianly loaded into the array. In some embodiments, a self-assembling hydrogel is generated on top of each cell, for example, using PEG x4 dendrimer DBCO and PEG 10 kda azide and a heterobifunctional linkage such as DBCO NHS for initial attachment to the cells or array position. Additional molecules may be incorporated in the hydrogel for capture of desired targets. In some embodiments, Protein G is attached for antibody capture, or poly dT oligonucleotides are attached for mRNA capture. Cells in this matrix may then be incubated with molecules for capture of matrix bound agents and therefore labelled, such as primers, DNA molecules, protein antigens, or antibodies. In some embodiments, a lysis solution is added to the cells on the surface, the cells are lysed, and their contents captured within the hydrogel matrix. In some embodiments, various reagents are flowed over the surface, such as wash buffers to remove reagents from a prior step, whilst maintaining bound RNA. In some embodiments, new reagents for a next step are added in this manner, such as, for example a reverse transcriptase solution containing enzyme and suitable buffer for the synthesis of a cDNA library for each cell. In some embodiments, it may be preferable to replace the non-hydrogel aqueous phase with a hydrocarbon or fibrous oil phase to prevent diffusion of intracellular or extracellular bound materials out of the matrix.

In some embodiments, the surface is patterned with hydrophilic spots on a hydrophobic or fibrous background. In this embodiment, droplets will self-assemble on the surface and be ready for subsequent reactions. These droplets may be used to generate hydrogels as well using click chemistry as described above. In some embodiments, the spots are on the order of the size of a cell and single cells can be captured in a nonpoissonian manner. In some embodiments, the spots are much larger than a single cell and capture of single cells occurs in a poissonian fashion. In some embodiments, patterning is random rather than arrayed though this may result in lower loading densities.

In some embodiments, each spot contains a plurality of poly-dt primers with the same 5' random DNA barcode so that each cell's mRNA can be specifically labelled. In some embodiments, a patterned surface is used to first capture a single bead that is smaller than the cell, but larger than the capture site. For example, a capture site of 1 um combined with a bead size of 2 um. In some embodiments, the beads are functionalized so that they can attach to both a cell and the capture site. For example, the beads can be coated with NHS and DBCO, while the capture sites have an azide. After attachment of beads to the capture site, cells are flowed so that each bead captures a single cell.

Once the cells are arrayed, it may be advantageous to transfer them to a microwell array containing other reagents for additional workup, such as lysis and capture of mRNA to primer coated beads. This enables non-poissonian loading of cells and/or beads to a microwell array.

These techniques can be used to capture single cells for RNA capture on barcoded beads, or to exactly position a single bead at each capture site for additional workup. For example, barcoded cDNA on a bead may be put on the capture array so that a single bead is at each spot. In some embodiments, a PCR reaction may be performed that amplifies the barcoded section of each molecule and amplifies a particular region of a subset of molecules of interest (for instance heavy and light chains), then links the barcode to the particular region of interest via ligation or assembly PCR. In this manner a sequencing read will contain the region of interest and the barcode and not be subject to the barcode being on the 5' or 3' ends of a molecule longer than the sequencing read length.

Sequencing of Immune Binding Proteins

Figure 1B:
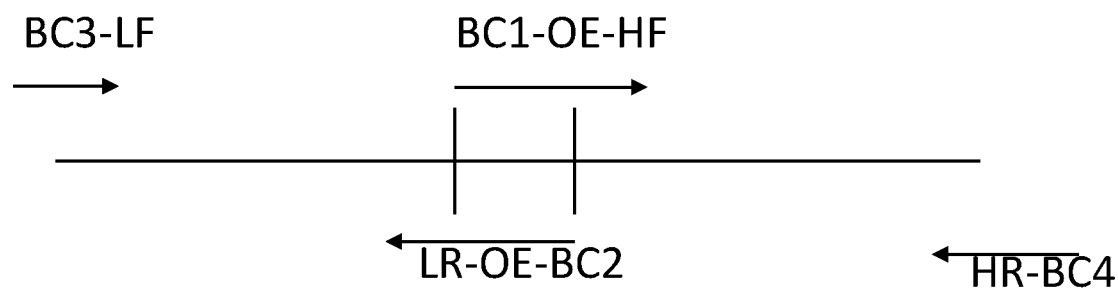

In some embodiments, the amplified nucleic acids are used in a sequencing reaction and the OE region can be flanked by one or more barcode regions (BC1 and BC2) (FIG. 1b). In some embodiments, the nucleic acids encoding the multiple chains of the immune binding protein are sequenced to identify the chains which form the immune binding protein (e.g., the heavy and light chains of an antibody).

Sequencing tools, methods, apparati, and reagents are well known to the person of ordinary skill in the art and include, for example, single-molecule real-time sequencing (Pacific Biosciences), ion semiconductor (Ion Torrent sequencing of Thermo Fisher), pyrosequencing (454 Life Sciences of Roche Diagnostics), sequencing by synthesis (Illumina), sequencing by ligation (SOLiD sequencing, Thermo Fisher), DNA nanoball sequencing (Complete Genomics), heliscope sequencing (Helicos Biosciences), and chain termination (Sanger sequencing). Sequencing machines and reagents are commercially available for all of these techniques, including for example, from Pacific Biosciences, Thermo Fisher, Roche Diagnostics, Illumina, Complete Genomics, and Helicos Biosciences.

In some embodiments, the resulting sequences are characterized for putative lineage information based on sequence alignment. In some embodiments, the sequence information is analyzed for similarity scores between sequences using bioinformatics tools (e.g. BLAST), and then optionally grouped into a phylogeny tree based on this information.

In some embodiments, sequences are compared using techniques well known to the person of ordinary skill in the art, including, for example, the local homology algorithm of Smith and Waterman, *Adv Appl Math.* 2:482, 1981; the homology alignment algorithm of Needleman and Wunsch, *J Mol Biol.* 48:443, 1970; the search for similarity method of Pearson and Lipman, *Proc Natl Acad Sci. USA* 85:2444, 1988; computerized implementations of these algorithms (GAP, BESTFIT, FASTA, and TFASTA in the GCG Wisconsin Software Package), or visual inspection (see generally, Current Protocols in Molecular Biology, F. M. Ausubel et al., eds., Greene Publishing Associates, Inc. and John Wiley & Sons, Inc., (1995 Supplement). Examples of algorithms that are suitable for comparing percent sequence identity and sequence similarity are the BLAST and BLAST 2.0 algorithms, which are described in Altschul et al., *J. Mol. Biol.* 215:403-410, 1990; and Altschul et al., *Nucleic Acids Res.* 25(17):3389-3402, 1977; respectively. Software for performing BLAST analyses is publicly available through the National Center for Biotechnology Information website. BLAST for nucleotide sequences can use the BLASTN program with default parameters, e.g., a wordlength (W) of 11, an expectation (E) of 10, M=5, N=−4, and a comparison of both strands. BLAST for amino acid sequences can use the BLASTP program with default parameters, e.g., a wordlength (W) of 3, an expectation (E) of 10, and the BLOSUM62 scoring matrix (see Henikoff and Henikoff, *Proc Natl Acad Sci. USA* 89:10915, 1989). Exemplary determination of sequence alignment and % sequence identity can also employ the BESTFIT or GAP programs in the GCG Wisconsin Software package (Accelrys, Madison Wis.), using default parameters provided.

Repertoires of Immune Binding Proteins

The invention relates to nucleic acids encoding immune binding proteins that preserve the in vivo multimeric associations of the immune polypeptide chains making up the immune binding protein (e.g., antibodies, T-lymphocyte receptors or innate immunity receptors). In some embodiments, immune binding protein libraries of the invention are enriched for nucleic acids encoding multimers that are functional polypeptides representing the multimeric complexes found in the repertoire from which the immune binding protein library was obtained.

In some embodiments, the nucleic acids represent the antibody repertoire of a subject who has become immune to an infectious disease, cancer, or other immunogenic challenge. In some embodiments, the nucleic acids represent the antibody repertoire of a subject who has had an immune reaction to an infectious disease, cancer, or other immunogenic challenge. In some embodiments, the antibody repertoire is from a subject that is naive for the target antigen. In some embodiments, the antibody repertoire represents the germ line repertoire of a subject or species. In some embodiments, the nucleic acids encoding the heavy and light chains of the antibody are combined in appropriate combinatorial fashion to generate a repertoire of antigen binding domains from the heavy and light chains.

In some embodiments, the repertoire represents the T-cell receptor repertoire of a subject who has become immune to an infectious disease, cancer, or other immunogenic challenge. In some embodiments, the nucleic acids represent the T-cell receptor repertoire of a subject who has had an immune reaction to an infectious disease, cancer, or other immunogenic challenge. In some embodiments, the T-cell receptor repertoire is from a subject that is naive for the target antigen. In some embodiments, the T-cell receptor repertoire represents the germ line repertoire of a subject or species. In some embodiments, the nucleic acids encoding the alpha, beta, gamma and zeta chains of the T-cell receptor are combined in appropriate combinatorial fashion to generate a repertoire of antigen binding domains from the T-cell receptor chains.

In some embodiments, the nucleic acids represent the innate immunity receptor repertoire of a subject who has become immune to an infectious disease, cancer, or other immunogenic challenge. In some embodiments, the nucleic acids represent the innate immunity receptor repertoire of a subject who has had an immune reaction to an infectious disease, cancer, or other immunogenic challenge. In some embodiments, the innate immunity receptor repertoire is from a subject that is naive for the target antigen. In some embodiments, the innate immunity receptor repertoire represents the germ line repertoire of a subject or species.

In some embodiments, the nucleic acids encoding the polypeptide chains for immune binding proteins are derived from individuals whom have mounted an immune response relevant to, for example, an infectious disease, a cancer, an autoimmune disease, an allergy, or a neurodegenerative disease. In some embodiments, the infectious disease is caused by an influenza virus. In some embodiments, the infectious disease is caused by a virus such as, for example, HIV, Ebola, Zika, HSV, RSV, or CMV.

Homologs of immune binding polypeptides of the invention are intended to be within the scope of the present invention. As used herein, the term "homologs" includes analogs and paralogs. The term "anologs" refers to two polynucleotides or polypeptides that have the same or similar function, but that have evolved separately in unrelated host organisms. The term "paralogs" refers to two polynucleotides or polypeptides that are related by duplication within a genome. Paralogs usually have different functions, but these functions may be related. Analogs and paralogs of an immune binding protein can differ from the immune binding protein by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the immune binding protein or its polynucleotide sequences, and will exhibit a similar function. Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same genetic locus in those species. Any and all such nucleic acid variations and resulting amino acid polymorphisms or variations that are the result of natural allelic variation and that do not alter the functional activity of the immune binding protein, are intended to be within the scope of the invention.

As used herein, the term "derivative" or "variant" refers to an immune binding protein, or a nucleic acid encoding an immune binding protein, that has one or more conservative amino acid variations or other minor modifications such that the corresponding polypeptide has substantially equivalent function when compared to the wild type polypeptide. These variants or derivatives include polypeptides having minor modifications of the immune binding protein primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions as an immune binding protein. The term "variant" also includes modification of a polypeptide where the native signal peptide is replaced with a heterologous signal peptide to facilitate the expression or secretion of the polypeptide from a host species.

The immune binding proteins of the invention also may include amino acid sequences for introducing a glycosylation site or other site for modification or derivatization of the polypeptide. In an embodiment, the polypeptides of the invention describe above may include the amino acid sequence N-X-S or N-X-T that can act as a glycosylation site. During glycosylation, an oligosaccharide chain is attached to asparagine (N) occurring in the tripeptide sequence N-X-S or N-X-T, where X can be any amino acid except Pro. This sequence is called a glycosylation sequon. This glycosylation site may be placed at the N-terminus, C-terminus, or within the internal sequence of the protein sequence used for the polypeptide of the invention.

Display Libraries of the Immune Binding Proteins

In some embodiments, the nucleic acids encoding immune binding proteins of the invention are engineered into vectors for displaying the immune binding protein on the surface of a cell or a viral particle. In some embodiments, repertoires of immune binding proteins (e.g., antibodies, T-cell receptors, or innate immunity receptors) are displayed on filamentous bacteriophage (e.g., McCafferty et al., 1990, Nature 348:552-554, which is incorporated by reference in its entirety for all purposes), yeast cells (e.g., Boder and Wittrup, 1997, Nat Biotechnol 15:553-557, which is incorporated by reference in its entirety for all purposes), and ribosomes (e.g., Hanes and Pluckthun, 1997, Proc Natl Acad Sci USA 94:4937-4942, which is incorporated by reference in its entirety for all purposes). Other embodiments of phage display are disclosed in, for example, U.S. Pat. Nos. 5,750,373, 5,733,743, 5,837,242, 5,969,108, 6,172,197, 5,580,717, and 5,658,727, all of which are incorporated by reference in their entirety for all purposes.

In some embodiments, phage display libraries are used to make human antibodies, T-cell receptors (or parts thereof), or innate immunity receptors (or parts thereof) from immunized humans, non-immunized humans, germ line sequences, or naive repertoires (Barbas & Burton, Trends Biotech (1996), 14:230; Griffiths et al., EMBO J. (1994), 13:3245; Vaughan et al., Nat. Biotech. (1996), 14:309; Winter EP 0368 684 B1, all of which are incorporated by reference in their entirety for all purposes). In some embodiments, naive, or nonimmune, antigen binding libraries are generated using a variety of lymphoidal tissues. Some of these libraries are commercially available, such as those developed by Cambridge Antibody Technology and Morphosys (Vaughan et al. (1996) Nature Biotech 14:309; Knappik et al. (1999) J. Mol. Biol. 296:57, all of which are incorporated by reference in their entirety for all purposes).

In some embodiments, Fab molecules can be displayed on phage if one of the chains (heavy or light) is fused to g3 capsid protein and the complementary chain exported to the periplasm as a soluble molecule. The two chains can be encoded on the same or on different replicons; the two antibody chains in each Fab molecule assemble post-translationally and the dimer is incorporated into the phage particle via linkage to one of the chains of g3p (see, e.g., U.S. Pat. No. 5,733,743, which is incorporated by reference in its entirety for all purposes). Alternatively, a scFv can be fused to a g3 capsid protein for display on the phage particle.

In some embodiments, nucleic acids encoding repertoires of immune binding proteins are engineered into vectors for display on bacterial, yeast, or mammalian cells. In some embodiments, bacterial, yeast or mammalian cells displaying immune binding proteins of the invention are contacted with a fluorescently labeled antigen, cells that bind the fluorescently labeled antigen will be fluorescent, and can then be isolated using fluorescence-activated cell sorting. In some embodiments, panning approaches are used to associate immune binding proteins with antigens bound by the immune binding protein.

In some embodiments, a library of immune binding proteins is engineered into a phage display vector and transformed into cells to generate phage which display the immune binding protein of interest in a fusion with one of the phage coat proteins. The phage library can be contacted with (aka panned against) a surface (e.g. a microtiter plate) that is coated with test antigens of interest. The plate is then washed one or more times with buffer. Phage that contain antibody variants that bind to the antigen of interest will be retained, whereas those that do not bind to the antigen will be washed away. The resulting phage library can subsequently be transformed into other host cells for further screening or replication and/or characterized by sequencing.

In some embodiments, the heavy chain/light chain pair of an antibody can be inserted into a surface display vector and cells can be transformed with this vector to display the antibody on the surface. Separately, a set of one or more antigens can be linked to a set of identifying nucleic acid barcode sequences such that each different antigen is linked to a unique sequence. The linkage can be done chemically or alternatively by cloning a set of barcoded antigens into a suitable display vector and expressing the antigen on the surface of phage or cells. The antigen set, now linked to a nucleic acid identifier, can then be contacted with the cells which display antibody on the surface. After the incubation, the individual cells can be isolated via emulsion, single-cell sorting, or other means. The resulting isolate will consist of a single cell displaying a homogeneous antibody on its surface, bound to one or more of the barcoded antigens. The nucleic acids coding for the antibody heavy chain, light chain, and antigen barcode, can then be amplified together and sequenced. The resulting sequence information will yield antibody/antigen coupling information. For example, if one antibody binds exclusively to a single antigen, the resulting sequence information will yield a unique antibody/antigen sequence. If an antibody binds a plurality of antigens, it will yield a mixed population of antibody/antigen coupled sequences. Thus, the relative specificity of each antibody in the population with respect to a set of antigens can be determined. Moreover, the relative abundance of the different coupled species can be correlated to the relative affinity of an antibody to each of the antigens in a panel.

In some embodiments, the pair can be cloned into a chimeric antigen receptor. A chimeric antigen receptor construct consists of at least a binding region (typically an scFv) and an intracellular signaling region. It may additionally contain other components such as a transmembrane region, a spacer/linker region, multiple signaling regions, and/or protein targeting and translocation sequences. Chimeric antigen receptors are well known in the art as described in, for example, U.S. patent application US20140242701, and U.S. Pat. Nos. 5,359,046, 5,686,281 and 6,103,521, which are incorporated by reference in their entirety for all purposes. The construct is placed into cells and the receptor is expressed, typically though not necessarily on the surface of a mammalian T cell. Upon the scFv binding to an antigen, the signaling domain initiates a cascade of events that ultimately results in transcription and activation of genes. In one example, the cell is further modified with a construct that expresses a marker protein, such as a fluorescent protein, luminescent protein, enzyme, or selectable marker that allows differentiation between that cell and other non-activated cells in the population. Thus, a population of cells containing a library of antibody constructs can be screened for those cells which are activated by binding to a target.

Immune Binding Protein and Antigens

Immune binding proteins bind a very diverse spectrum of antigens, with varying levels of affinity and specificity. In some embodiments, immune binding proteins bind very specific antigens, while other immune binding proteins bind a broader array of antigens. Depending on the application, either one of these options may be desired. For example, an immune binding protein that can recognize multiple strains of influenza would have benefit against may strains of influenza, whereas an immune binding protein for an anti-tumor therapy may need to bind only one very specific conformation of an antigen, to avoid attacking normal versions of the antigen present on healthy cells and tissues.

In some embodiments, a repertoire of immune binding proteins (e.g., antibodies, T-cell receptors, and/or innate immunity receptors) made by the methods of the invention is screened against a panel of antigens. In some embodiments, each member of the panel of antigens is labeled with nucleic acids encoding unique bar codes for each antigen. In some embodiments, the screening of multiple antigens is followed by amplification reactions that produce nucleic acids encoding the polypeptide chains of the immune binding protein (e.g., the heavy and light chains of an antibody)

and the antigen (e.g., if the antigen is a polypeptide) or a nucleic acid bar code for the antigen. In some embodiments, immune binding proteins are displayed on a cell surface and screened against a panel of bar-coded antigens. Those cells with displayed immune binding proteins that bind an antigen are place in microwells (single cell in each microwell) and/or capture in an emulsion, and amplification reactions are performed to make nucleic acids encoding the chains of the immune binding protein and the bar code of the antigen.

Figure 1C:
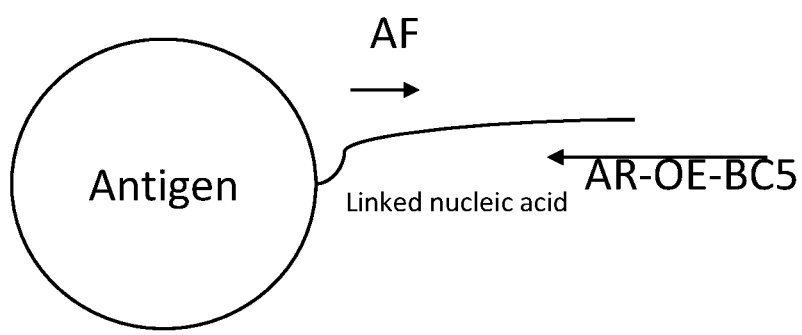

In some embodiments, an amplification reaction as describe above for an immune protein is used adding a set of forward and reverse primers for amplification of the nucleic acid attached to the antigen (AF and AR) (FIG. 1C). In some embodiments, the AR primer additionally contains a barcode (BC5) and an OE region matching that of a primer for a nucleic acid encoding one of the chains of the immune protein (e.g., the LF primer for an antibody). The amplification is carried out, resulting in a mixture of nucleic acids encoding the immune protein (e.g., HC/LC molecules) and nucleic acids encoding a chain of the immune protein and the nucleic acid for identifying the antigen (e.g., HC/Antigen molecules). In some embodiments, these molecules are sequenced using high-throughput methods, and the resulting information identifies antigens with individual immune binding proteins (e.g., antibodies).

In some embodiments, a second overlap extension (OE) is placed on the BR and immune protein primers (e.g., for an antibody the LF primer). In this embodiment, following amplification one obtains a nucleic acid encoding the chains for the immune binding protein (e.g., heavy and light chains of an antibody), and the bar code for the antigen. In some embodiments, this multipartite nucleic acid is sequenced to identify the immune binding protein, and the antigens to which the immune binding protein bound.

Nucleic Acids

In some embodiments, the present invention relates to the nucleic acids that encode, at least in part, the individual peptides, polypeptides, proteins, and RNA control devices of the present invention. In some embodiments, the nucleic acids may be natural, synthetic or a combination thereof. The nucleic acids of the invention may be RNA, mRNA, DNA or cDNA.

In some embodiments, the nucleic acids of the invention also include expression vectors, such as plasmids, or viral vectors, or linear vectors, or vectors that integrate into chromosomal DNA. Expression vectors can contain a nucleic acid sequence that enables the vector to replicate in one or more selected host cells. Such sequences are well known for a variety of cells. The origin of replication from the plasmid pBR322 is suitable for most Gram-negative bacteria. In eukaryotic host cells, e.g., mammalian cells, the expression vector can be integrated into the host cell chromosome and then replicate with the host chromosome. Similarly, vectors can be integrated into the chromosome of prokaryotic cells.

Expression vectors also generally contain a selection gene, also termed a selectable marker. Selectable markers are well-known in the art for prokaryotic and eukaryotic cells, including host cells of the invention. Generally, the selection gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. In some embodiments, an exemplary selection scheme utilizes a drug to arrest growth of a host cell. Those cells that are successfully transformed with a heterologous gene produce a protein conferring drug resistance and thus survive the selection regimen. Other selectable markers for use in bacterial or eukaryotic (including mammalian) systems are well-known in the art.

In some embodiments, an example of a promoter that is capable of expressing a transgene encoding an immune binding protein of the invention in a mammalian host cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving expression from transgenes cloned into a lentiviral vector. See, e.g., Milone et al., Mol. Ther. 17(8): 1453-1464 (2009), which is incorporated by reference in its entirety for all purposes. Another example of a promoter is the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to the simian virus 40 (SV40) early promoter, mouse mammary tumor virus promoter (MMTV), human immunodeficiency virus (HIV) long terminal repeat (LTR) promoter, MoMuLV promoter, phosphoglycerate kinase (PGK) promoter, MND promoter (a synthetic promoter that contains the U3 region of a modified MoMuLV LTR with myeloproliferative sarcoma virus enhancer, see, e.g., Li et al., J. Neurosci. Methods vol. 189, pp. 56-64 (2010) which is incorporated by reference in its entirety for all purposes), an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter. Further, the invention is not limited to the use of constitutive promoters.

Inducible promoters are also contemplated as part of the invention. Examples of inducible promoters include, but are not limited to a metallothionine promoter, a glucocorticoid promoter, a progesterone promoter, a tetracycline promoter, a c-fos promoter, the T-REx system of ThermoFisher which places expression from the human cytomegalovirus immediate-early promoter under the control of tetracycline operator(s), and RheoSwitch promoters of Intrexon. Karzenowski, D. et al., BioTechiques 39:191-196 (2005); Dai, X. et al., Protein Expr. Purif 42:236-245 (2005); Palli, S. R. et al., Eur. J. Biochem. 270:1308-1515 (2003); Dhadialla, T. S. et al., Annual Rev. Entomol. 43:545-569 (1998); Kumar, M. B, et al., J. Biol. Chem. 279:27211-27218 (2004); Verhaegent, M. et al., Annal. Chem. 74:4378-4385 (2002); Katalam, A. K., et al., Molecular Therapy 13:S103 (2006); and Karzenowski, D. et al., Molecular Therapy 13:S194 (2006), U.S. Pat. Nos. 8,895,306, 8,822,754, 8,748,125, 8,536,354, all of which are incorporated by reference in their entirety for all purposes.

Expression vectors of the invention typically have promoter elements, e.g., enhancers, to regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

In some embodiments, control regions suitable for a bacterial host cells are used in the expression vector. In some embodiments, suitable control regions for directing transcription of the nucleic acid constructs of the invention, include the control regions obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and the prokaryotic beta-lactamase gene, the tac promoter, or the T7 promoter.

In some embodiments, control regions for filamentous fungal host cells, include control regions obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid control regions thereof. Exemplary yeast cell control regions can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase.

In some embodiments, exemplary control regions for insect cells include, among others, those based on polyhedron, PCNA, OpIE2, OpIE1, Drosophila metallothionein, and Drosophila actin 5C. In some embodiments, insect cell promoters can be used with Baculoviral vectors.

In some embodiments, exemplary control regions for plant cells include, among others, those based on cauliflower mosaic virus (CaMV) 35S, polyubiquitin gene (PvUbi1 and PvUbi2), rice (*Oryza sativa*) actin 1 (OsAct1) and actin 2 (OsAct2) control regions, the maize ubiquitin 1 (ZmUbi1) control region, and multiple rice ubiquitin (RUBQ1, RUBQ2, rubi3) control regions.

In some embodiments, the expression vector contains one or more selectable markers, which permit selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*.

In some embodiments, it may be desirable to modify the polypeptides of the present invention. One of skill will recognize many ways of generating alterations in a given nucleic acid construct to generate variant polypeptides Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see, e.g., Gillam and Smith, *Gene* 8:81-97, 1979; Roberts et al., *Nature* 328:731-734, 1987, which is incorporated by reference in its entirety for all purposes). In some embodiments, the recombinant nucleic acids encoding the polypeptides of the invention are modified to provide preferred codons which enhance translation of the nucleic acid in a selected organism.

The polynucleotides of the invention also include polynucleotides including nucleotide sequences that are substantially equivalent to the polynucleotides of the invention. Polynucleotides according to the invention can have at least about 80%, more typically at least about 90%, and even more typically at least about 95%, sequence identity to a polynucleotide of the invention. The invention also provides the complement of the polynucleotides including a nucleotide sequence that has at least about 80%, more typically at least about 90%, and even more typically at least about 95%, sequence identity to a polynucleotide encoding a polypeptide recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions which can routinely isolate polynucleotides of the desired sequence identities.

Nucleic acids which encode protein analogs or variants in accordance with this invention (i.e., wherein one or more amino acids are designed to differ from the wild type polypeptide) may be produced using site directed mutagenesis or PCR amplification in which the primer(s) have the desired point mutations. For a detailed description of suitable mutagenesis techniques, see Sambrook et al., Molecular Cloning: A Laboratory Manual, Cold Spring Harbor Laboratory Press, Cold Spring Harbor, N.Y. (1989) and/or Current Protocols in Molecular Biology, Ausubel et al., eds, Green Publishers Inc. and Wiley and Sons, N.Y (1994), each of which is incorporated by reference in its entirety for all purposes. Chemical synthesis using methods well known in the art, such as that described by Engels et al., *Angew Chem Intl Ed.* 28:716-34, 1989 (which is incorporated by reference in its entirety for all purposes), may also be used to prepare such nucleic acids.

In some embodiments, amino acid "substitutions" for creating variants are preferably the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

The nucleic acid of the present invention can be linked to another nucleic acid so as to be expressed under control of a suitable promoter. The nucleic acid of the present invention can be also linked to, in order to attain efficient transcription of the nucleic acid, other regulatory elements that cooperate with a promoter or a transcription initiation site, for example, a nucleic acid comprising an enhancer sequence, a polyA site, or a terminator sequence. In addition to the nucleic acid of the present invention, a gene that can be a marker for confirming expression of the nucleic acid (e.g. a drug resistance gene, a gene encoding a reporter enzyme, or a gene encoding a fluorescent protein) may be incorporated.

When the nucleic acid of the present invention is introduced into a cell ex vivo, the nucleic acid of the present invention may be combined with a substance that promotes transference of a nucleic acid into a cell, for example, a reagent for introducing a nucleic acid such as a liposome or a cationic lipid, in addition to the aforementioned excipients. Alternatively, a vector carrying the nucleic acid of the present invention is also useful. Particularly, a composition in a form suitable for administration to a living body which contains the nucleic acid of the present invention carried by a suitable vector is suitable for in vivo gene therapy.

Host Cells

In some embodiments, nucleic acids encoding an immune binding protein of the invention (e.g., an antibody) are cloned into an appropriate expression vector for expression of immune binding protein in a host cell. In some embodiments, the host cells of the invention include, for example, bacterial, fungi, or mammalian host cells. In some embodiments, the host cell is a bacterium, including, for example, *Bacillus*, such as *B. lichenformis* or *B. subtilis*; *Pantoea*, such as *P. citrea*; *Pseudomonas*, such as *P. alcaligenes*; *Streptomyces*, such as *S. lividans* or *S. rubiginosus*; *Escherichia*, such as *E. coli*; *Enterobacter*; *Streptococcus*; *Archaea*, such as *Methanosarcina mazei*; or *Corynebacterium*, such as *C. glutamicum*.

In some embodiments, the host cells are fungi cells, including, but not limited to, fungi of the genera *Saccharomyces, Klyuveromyces, Candida, Pichia, Debaromyces, Hansenula, Yarrowia, Zygosaccharomyces,* or *Schizosaccharomyces*. In some embodiments, the host cell is a fungi, including, among others, *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizobus oryzae, Yarrowia lipolytica,* and the like. In some embodiments, the eukaryotic cells are algal, including but not limited to algae of the genera Chlorella, Chlamydomonas, Scenedesmus, Isochrysis, Dunaliella, Tetraselmis, Nannochloropsis, or Prototheca. In some embodiments, the algae is a green algae, red algae, glaucophytes, chlorarachniophytes, euglenids, chromista, or dinoflagellates.

In some embodiments, the eukaryotic cells are mammalian cells, such as mouse, rat, rabbit, hamster, porcine, bovine, feline, or canine. In some embodiments, the mammalian cells are cells of primates, including but not limited to, monkeys, chimpanzees, gorillas, and humans. In some embodiments, the mammalians cells are mouse cells, as mice routinely function as a model for other mammals, most particularly for humans (see, e.g., Hanna, J. et al., *Science* 318:1920-23, 2007; Holtzman, D. M. et al., *J Clin Invest.* 103 (6):R15-R21, 1999; Warren, R. S. et al., *J Clin Invest.* 95: 1789-1797, 1995; each publication is incorporated by reference in its entirety for all purposes). In some embodiments, animal cells include, for example, fibroblasts, epithelial cells (e.g., renal, mammary, prostate, lung), keratinocytes, hepatocytes, adipocytes, endothelial cells, and hematopoietic cells. In some embodiments, the animal cells are adult cells (e.g., terminally differentiated, dividing or non-dividing) or embryonic cells (e.g., blastocyst cells, etc.) or stem cells. In some embodiments, the animal cell is a cell line derived from an animal or other source.

In some embodiments, the mammalian cell is a cell found in the circulatory system of a mammal, including humans. Exemplary circulatory system cells include, among others, red blood cells, platelets, plasma cells, T-cells, natural killer cells, B-cells, macrophages, neutrophils, or the like, and precursor cells of the same. As a group, these cells are defined to be circulating eukaryotic cells of the invention. In some embodiments, the mammalian cells are derived from any of these circulating eukaryotic cells. The present invention may be used with any of these circulating cells or cells derived from the circulating cells. In some embodiments, the mammalian cell is a T-cell or T-cell precursor or progenitor cell. In some embodiments, the mammalian cell is a helper T-cell, a cytotoxic T-cell, a memory T-cell, a regulatory T-cell, a natural killer T-cell, a mucosal associated invariant T-cell, a gamma delta T cell, or a precursor or progenitor cell to the aforementioned. In some embodiments, the mammalian cell is a natural killer cell, or a precursor or progenitor cell to the natural killer cell. In some embodiments, the mammalian cell is a B-cell, or a plasma cell, or a B-cell precursor or progenitor cell. In some embodiments, the mammalian cell is a neutrophil or a neutrophil precursor or progenitor cell. In some embodiments, the mammalian cell is a megakaryocyte or a precursor or progenitor cell to the megakaryocyte. In some embodiments, the mammalian cell is a macrophage or a precursor or progenitor cell to a macrophage.

In some embodiments, a source of cells is obtained from a subject. The subject may be any living organism. Examples of subjects include humans, dogs, cats, mice, rats, and transgenic species thereof. In some embodiments, T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available in the art, may be used. In some embodiments, T cells can be obtained from a unit of blood collected from a subject using any number of techniques known to the skilled artisan, such as Ficoll separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In an alternative aspect, the wash solution lacks calcium and may lack magnesium or may lack many if not all divalent cations. Initial activation steps in the absence of calcium can lead to magnified activation.

In some embodiments the plant cells are cells of monocotyledonous or dicotyledonous plants, including, but not limited to, alfalfa, almonds, asparagus, avocado, banana, barley, bean, blackberry, brassicas, broccoli, cabbage, canola, carrot, cauliflower, celery, cherry, chicory, citrus, coffee, cotton, cucumber, eucalyptus, hemp, lettuce, lentil, maize, mango, melon, oat, papaya, pea, peanut, pineapple, plum, potato (including sweet potatoes), pumpkin, radish, rapeseed, raspberry, rice, rye, sorghum, soybean, spinach, strawberry, sugar beet, sugarcane, sunflower, tobacco, tomato, turnip, wheat, zucchini, and other fruiting vegetables (e.g. tomatoes, pepper, chili, eggplant, cucumber, squash etc.), other bulb vegetables (e.g., garlic, onion, leek etc.), other pome fruit (e.g. apples, pears etc.), other stone fruit (e.g., peach, nectarine, apricot, pears, plums etc.), Arabidopsis, woody plants such as coniferous and deciduous trees, an ornamental plant, a perennial grass, a forage crop, flowers, other vegetables, other fruits, other agricultural crops, herbs, grass, or perennial plant parts (e.g., bulbs; tubers; roots; crowns; stems; stolons; tillers; shoots; cuttings, including un-rooted cuttings, rooted cuttings, and callus cuttings or callus-generated plantlets; apical meristems etc.). The term "plants" refers to all physical parts of a plant, including seeds, seedlings, saplings, roots, tubers, stems, stalks, foliage and fruits.

Applications

In some embodiments, the immune binding proteins of the invention are used in therapies for infectious diseases, cancer, allergies, and autoimmune diseases. In some embodiments, the methods of the invention are used to make repertoires of immune binding proteins from subjects that have been challenged/infected with an infectious agent. In some embodiments, the immune binding proteins of the invention are used in therapies to treat subjects infected with an infectious agent. In some embodiments, the immune binding proteins of the invention are used to treat subjects with cancer or allergies. In some embodiments, the immune binding proteins of the invention are used to treat melanoma, lymphoma, leukemia and other cancers responsive to immune therapy. In some embodiments, the immune binding proteins of the invention are used to treat cancers that respond to immune checkpoint inhibitor therapy. In some embodiments, addition of exogenous immune binding protein (e.g., antibody) helps the subject's body accelerate its own immune response to a pathogen, in effect "transplanting" the immunity from one individual to another. In some embodiments, the immune binding proteins of the invention are used prophylactically. In some embodiments, the immune binding proteins of the invention are used in diagnostic applications. In some embodiments, the immune binding proteins of the invention provide information on a subject's response to a therapy. In some embodiments, the immune binding proteins of the invention provide information on a subject's response to an antibody therapy, small molecule drug therapy, biologic therapy, or cellular immunotherapy.

In some embodiments, immune binding proteins (e.g., antibodies) can be obtained from the subject that neutralize an infectious agent or can be made to become neutralizing.

In some embodiments, the infectious agent is a bacterial strain of *Staphylococci, Streptococcus, Escherichia coli, Pseudomonas*, or *Salmonella*. In some embodiments, the infectious agent is a *Staphylococcus aureus, Neisseria gonorrhoeae, Streptococcus pyogenes*, Group A *Streptococcus*, Group B *Streptococcus* (*Streptococcus agalactiae*), *Streptococcus pneumoniae*, and *Clostridium tetani*. In some embodiments, the infectious agent is a bacterial pathogen that may infect host cells including, for example, *Helicobacter pyloris, Legionella pneumophilia*, a bacterial strain of *Mycobacteria* sps. (e.g. *M. tuberculosis, M. avium, M. intracellulare, M. kansaii*, or *M. gordonea*), *Neisseria meningitides, Listeria monocytogenes, R. rickettsia, Salmonella* spp., *Brucella* spp., *Shigella* spp., or certain *E. coli* strains or other bacteria that have acquired genes with invasive factors. In some embodiments, the infectious agent is a bacterial pathogen that is antibiotic resistant. In some embodiments, the infectious agent is a viral pathogen including, for example, Ebola, Zika, RSV, Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus.

In some embodiments, immune binding proteins of the invention are used to boost the immunity of a subject against an infectious disease. For example, in influenza the body responds within 7-10 days to a challenge; however, in immunocompromised patients such as the elderly, the immune response timing or extent may be insufficient to fight off the infection, resulting in severe complications and possibly death. By boosting the immune system with antibodies designed to fight the relevant strain of influenza, the infection in the subject can treated. In some embodiments, the methods of the invention are used to rapidly develop strain-specific antibodies to emerging pandemic strains of influenza. In some embodiments, immune binding proteins of the invention are used to treat infected patients and/or passively immunize vulnerable populations facing an outbreak. In some embodiments, the immune binding proteins are administered prophylactically. In some embodiments, the prophylactic administration of the immune binding proteins protect at risk groups of subjects from a disease.

In some embodiments, the infectious agent is a herpes simplex virus 1 (HSV-1), herpes simplex virus 2 (HSV-2), varicella zoster, Epstein-Barr, cytomegalovirus (CMV), or Kaposi's sarcoma viruses. HSV-1 primarily causes oral herpes, ocular herpes, and herpes encephalitis, and occasionally causes genital herpes; HSV-2 primarily causes genital herpes but can also cause oral herpes; varicella zoster causes chickenpox and shingles; Epstein-Barr causes mononucleosis and is associated with several cancers including Burkitt's lymphoma; CMV causes mononucleosis-like syndrome and congenital/neonatal morbidity and mortality. Some of the herpesviridae, and in particular HSV-1, have been associated with and proposed as causative agents for Alzheimer's Disease. In some embodiments, immune binding proteins of the invention can be used to treat and/or passively immunize against these herpesviridae. In some embodiments, an injection or topical application of an antibody against HSV-1 or HSV-2 can be employed to reduce the incidence or severity of the effects of herpes outbreaks.

In some embodiments, the immune binding proteins of the invention are useful for treating a cancer. In some embodiments, the cancer is a sarcoma, carcinoma, melanoma, chordoma, malignant histiocytoma, mesothelioma, glioblastoma, neuroblastoma, medulloblastoma, malignant meningioma, malignant schwannoma, leukemia, lymphoma, myeloma, myelodysplastic syndrome, myeloproliferative disease. In some embodiments, the cancer is a leukemia, lymphoma, myeloma, myelodysplastic syndrome, and/or myeloproliferative disease. In some embodiments, the cancer is one that is responsive to immunotherapy. In some embodiments, the cancer is one that is responsive to immune checkpoint inhibitor therapy.

In some embodiments, the immune binding proteins of the invention are specific for a tumor specific or enriched antigen. In some embodiments, examples of tumor specific or enriched antigens include, for example, one or more of 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD21, CD22, CD23 (IgE receptor), CD28, CD30 (TNFRSF8), CD33, CD4, CD40, CD44 v6, CD51, CD52, CD56, CD74, CD80, CEA, CNT0888, CTLA-4, DR5, EGFR, EpCAM, EphA3, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, L1-CAM, IL-13, IL-6, insulin-like growth factor I receptor, alpha 5β1-integrin, integrin αvβ3, MORAb-009, MS4A1, MUC1, mucin CanAg, N-glycolylneuraminic acid, NPC-1C, PDGF-Rα, PDL192, phosphatidylserine, prostatic carcinoma cells, RANKL, RON, ROR1, SCH 900105, SDC1, SLAMF7, TAG-72, tenascin C, TGF β2, TGF-β, TRAIL-R1, TRAIL-R2, tumor antigen CTAA16.88, VEGF-A, VEGFR-1, VEGFR2, 707-AP, ART-4, B7H4, BAGE, β-catenin/m, Bcr-abl, MN/C IX antibody, CAMEL, CAP-1, CASP-8, CD25, CDC27/m, CDK4/m, CT, Cyp-B, DAM, ErbB3, ELF2M, EMMPRIN, ETV6-AML1, G250, GAGE, GnT-V, Gp100, HAGE, HLA-A*0201-R1701, HPV-E7, HSP70-2M, HST-2, hTERT (or hTRT), iCE, IL-2R, IL-5, KIAA0205, LAGE, LDLR/FUT, MAGE, MART-1/melan-A, MART-2/Ski, MC1R, myosin/m, MUM-1, MUM-2, MUM-3, NA88-A, PAP, proteinase-3, p190 minor bcr-abl, Pml/RARα, PRAIVIE, PSA, PSM, PSMA, RAGE, RU1 or RU2, SAGE, SART-1 or SART-3, survivin, TPI/m, TRP-1, TRP-2, TRP-2/INT2, WT1, NY-Eso-1 or NY-Eso-B or vimentin.

In some embodiments, the tumor antigen-binding immune binding protein (e.g., antibody) can be used to make a chimeric antigen receptor specific for the tumor antigen and this CAR construct is placed into a T cell and/or a natural killer cell. In some embodiments the T-cell and/or natural killer cells with the tumor specific CAR are used to treat subjects with cancers that bear the tumor antigen.

In some embodiments, the immune binding proteins of the invention are useful for treating subjects with allergies. Common allergens include shellfish, nuts, milk, ollen, certain medications, latex, insect bites, and some plant compounds (e.g. urushiol). In some embodiments, the immune binding proteins of the invention bind the allergen of interest without triggering the allergic reaction. For example, the immune binding protein could be an antibody without an Fc region, or could be an antibody in an IgG format or other format that is not an IgE format. In these embodiments, the immune binding protein of the invention binds to the allergen without triggering an allergic reaction and this binding can prevent IgE antibody in the subject from binding to the allergen and causing the allergic reaction (this is a competitive inhibition reaction). In some embodiments, the immune binding protein which binds the allergen is obtained from the subject with the allergy.

In some embodiments, the immune binding proteins of the invention are useful for treating subjects with autoimmune diseases. In some embodiments, the autoimmune disease is rheumatoid arthritis, lupus, celiac disease, Sjorgren's syndrome, polymyalgia rheumatica, multiple sclerosis, ankylosing spondylitis, Type 1 diabetes, and the like. In some embodiments, the immune binding proteins of the invention bind the antigen target of the autoimmune disease without triggering the autoimmune reaction. For example, the immune binding protein could be an antibody without an Fc region, or could be an antibody in a format that does not interact with the effector cells that are associated with the autoimmune disease. In these embodiments, the immune binding protein of the invention binds to the autoimmune antigen without triggering an autoimmune reaction and this binding can prevent the subject's immune system from reacting with the autoimmune antigen reducing the autoimmune disease (this can be a competitive inhibition reaction).

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

EXAMPLES

Example 1. Multiplexed Antigen Staining of Primary Cells

In some embodiments, barcoded peptide antigens are prepared by incubating antigens with an NHS DBCO heterobifunctional crosslinker. Secondly a DNA oligo with a 5' primer site, a DNA barcode, a 3' primer site, a 3' poly dt, and containing a 3' biotin and a 5' azide are mixed with the peptide-DBCO antigens to make bar code labeled antigens.

In some embodiments, human B cells with membrane bound receptors are isolated using magnetic separation. Cells are incubated with the mixture of bar code labelled antigens so that labelled antigens bind membrane bound immunoglobulin receptors. The cells are washed and optionally the cells may be FACS sorted after incubating them with a streptavidin-PE fluorophore. In some embodiments, the cells are then single cell sorted into plates containing a Triton based lysis mixture and poly-dt primer with a 5' amplification tag. In some embodiments, a reverse transcription reaction is performed with a template switching reverse transcriptase, a template switch primer and appropriate buffer and dNTP mixture. The cDNA library with barcoded antigen is amplified with KAPA Hifi and primers specific to the amplification tag and the template switch sequence. In some embodiments, specific regions of interest, such as the heavy and light chain CDR regions and the antigen barcode, are amplified with primers containing a well-specific barcode and a 3' primer to the region of interest via PCR. In some embodiments, these fragments are used to generate a sequencing library for high throughput sequencing. After sequencing, the data is de-convoluted by identification of well specific barcodes, sequence assembly of heavy and light chain reads and identification of reads with antigen barcodes.

Example 2. Multiplexed Antigen Library Sequencing Using Beads

A pool of B-cells bound to antigens is made as described in Example 1. In some embodiments, following antigen staining and washing, cells are separated with a monodisperse droplet generator. In some embodiments, the droplets comprise lysis/binding mix containing one or more barcoded poly-dt capture beads (beads coated with a DNA primer containing a 5' amplification tag and a 3' poly dT sequence) in a high salt/detergent buffer and 1-10 cells. In some embodiments, an oil phase is used to make an emulsion which oil phase is a perflurocarbon containing an amphiphilic fluorous/aqueous surfactant. As the cells lyse, their RNA is captured on the barcoded poly-dt beads as is the barcoded antigen DNA. In some embodiments, the emulsion is broken under stringent binding conditions, such as with methylene chloride and 6×SSC buffer. The bead mixture is washed twice and resuspended in a reverse transcriptase reaction and incubated. In some embodiments, the beads ("template beads") are separated in another water/oil emulsion generated with a monodisperse droplet generator so that each droplet has about one "template bead" in a PCR mixture. The PCR mixture also contains one or more "prep" beads containing beads that are coated with primers containing a 5' amplification tag and a bead specific barcode. In some embodiments, the primers have a 3' poly dA, some have a 3' antigen primer, some have a 3' heavy chain reverse primer, and some have a 3' light chain reverse primer. In some embodiments, the aqueous phase has 5' heavy chain primers, 5' light chain primers, 5' antigen primers and the 5' amplification tag from the poly dT capture beads. Kapa Hifi is a suitable polymerase for this amplification. In some embodiments, following PCR the emulsion is broken and a high throughput sequencing library is generated. Following sequencing, all reads associated with the last round PCR barcodes are split into pools. Then, cell-specific barcodes are identified by the reads associated with the polyA/5' amplification tag. In some embodiments, all reads associated with beads containing the same cell-specific barcodes are grouped together. In some embodiments, these groups are used to provide the sequence or identification of the heavy chain, light chain and the antigen which associate together.

Example 3. Multiplexed Antigen Library Sequencing Using 5'5' Primers

A 5'5' primer is made by mixing a 5' DBCO oligonucleotide and a 5' azide oligonucleotide. In some embodiments, the DBCO and azide do not need to be at the precise 5' end of the component oligos but may be placed in a manner that still allows for the 3' end to perform a PCR reaction. The combined product is isolated from unreacted component oligos. In some embodiments, it may be higher yielding to use these 5'5' primers instead of beads for linking reads to cell-specific barcodes. In some embodiments, a reaction uses primers containing a 5'5' linkage with one of the 3' ends containing a polyA and the other containing a 3' light, 3' heavy or 3' antigen tag. In some embodiments, the reaction mix also contains 5' heavy, 5' light and 5' antigen and 5' amplification tag primers with 5' phosphate groups. In some embodiments, an emulsion is generated with a monodisperse emulsion generator so that each droplet contains about 1 "template bead" and the 5'5' primer mixture and KAPA hifi in a suitable buffer with dNTP's, etc. Following emulsion PCR, the emulsion is broken with methylene chloride, the aqueous phase extracted and cleaned. The DNA obtained is resuspended in ligation buffer with ligase. In some embodiments, the DNA obtained after ligation is treated with exonuclease(s). In some embodiments, the mixture obtained after exonuclease treatment is placed into a PCR with KAPA hifi for 20 cycles with the 3' polyA primer, 3' heavy primer and 3' light primer. In some embodiments, the PCR product is used as a template to generate a sequencing library which is sequenced on a high throughput sequencer. Following sequencing, the reads are grouped according to their cell-specific barcode and then reads for heavy, light and antigen are identified.

Example 4. Multiplexed Gene Specific Bead Libraries With PCR

In some embodiments, bead libraries are made where each bead has primers containing a bead specific barcode, molecule specific barcode and a plurality of gene specific primers. In some embodiments, MyOne carboxylate dynabeads are first coated with a 5' amplification primer sequence. The beads are incubated with a limited dilution of DNA primers containing the reverse complement amplification sequence at the 3' end, a unique molecular barcode comprising 12 N residues, and an adapter sequence of 12 bases (for example the M13 sequencing primer sequence). After incubating the beads with this mixture, the beads are pelleted and washed, and then placed in a Klenow exo-polymerase reaction. The beads are then pelleted and washed.

In some embodiments, the beads are resuspended into a PCR mixture containing polymerase and a soluble version of the reverse complement adapter sequence and placed into an oil/aqueous emulsion using a monodisperse droplet generator. Following droplet generation, the emulsion is cycled for 30× and then broken. The beads are then reacted with T7 exonuclease. Then the beads are placed in a reaction mixture containing oligonucleotides with the 3' reverse complement adapter sequence, a 10 base random DNA sequence, and a 5' adapter 2 sequence and a klenow exo-polymerase mix. In some embodiments, following this reaction, the beads are treated with T7 exonuclease. In an alternate embodiment, heat is used to remove the second strand instead of a nuclease. In some embodiments, the beads are then placed in a mixture containing capture primers with a 3' reverse complement of adapter 2, and a 5' reverse complement of the 3' heavy, 3' light chain and 3' antigen tag are added with a klenow exo-polymerase mix. In some embodiments, following this reaction the beads are treated with T7 exonuclease.

Example 5. Multiplexed Gene Specific Bead Libraries With Ligation

In some embodiments, bead libraries are made where each bead has primers containing a bead specific barcode, molecule specific barcode and a plurality of gene specific primers. In some embodiments, MyOne carboxylate dynabeads are first coated with a 5' amplification primer sequence with a 5' amino moiety. The beads are then incubated with a limited dilution of DNA primers containing the reverse complement amplification sequence at the 3' end, a unique molecular barcode comprising 12 N residues, and an adapter sequence of 12 bases (for example the M13 sequencing primer sequence). After incubating the beads with this mixture, the beads are treated with Klenow exo-polymerase. In some embodiments, the beads are then mixed with a soluble version of the reverse complement adapter sequence and placed into an oil/aqueous emulsion using a monodisperse droplet generator. Following droplet generation, the emulsion is cycled for 30× and then broken.

The beads are placed in a mixture with double stranded DNA sequence with the forward strand containing a 5' phosphate, 10 base random DNA sequence, and the 3' heavy primer, 3' light chain primer or 3' antigen tag primer at the 3' end. The mixture also contains T4 DNA ligase. After this reaction, the beads are treated with T7 exonuclease.

Example 6. Preparation of B Cells With Membrane Bound Receptors

In some embodiments, it may be beneficial to increase the receptor density on cells. In some embodiments, primary B cells are transformed into antibody secreting plasma cells by incubation with IL21, IL4, and CD40L. These cells are treated with an NHS-azide heterobifunctional crosslinker. Protein-G DBCO is prepared by mixing protein G with an NHS-DBCO heterobifunctional crosslinker. The cells are treated with the protein-G DBCO with additional protein-G and then spatially separated in a microwell array with soluble or solid phase protein-G in the buffer. The cells are centrifuged or gravity settled into the bottom of each well. The cells are removed from the microwell by centrifugation or gravity and placed in a solution with a metabolic inhibitor such as present in many commonly available stain buffers. Following this treatment, the cells are reacted with antigens.

Example 7. Preparation of B Cells With Hydrogel Bound Receptors

In some embodiments, it may be beneficial to further increase the receptor density on the antigen binding cells. In some embodiments, primary B cells are transformed into antibody secreting plasma cells by incubation with IL21, IL4, and CD40L. The cells are treated with an NHS-azide heterobifunctional crosslinker and then spatially separated in a microwell array. The cells in the microwells are treated with an DBCO 4× dendrimer PEG, and then treated with an azide-azide homobifunctional lkd PEG. In some embodiments, the DBCO 4× dendrimer PEG treatment and the homobifunctional azide-azide lkda PEG treatment are repeated for a desired number of rounds. These additional cycles of DBCO/azide pegs create additional functionalization sites and larger hydrogel volume for better signal until a desired amount of functionalization and/or hydrogel is produced. In some embodiments, Protein-G DBCO is prepared by mixing protein G with an NHS-DBCO heterobifunctional crosslinker. The cells embedded in hydrogel are treated with the protein-G DBCO with additional protein-G. The cells are removed from the microwell and placed in a solution with a metabolic inhibitor such as present in many commonly available stain buffers. The cells are ready for reaction with antigens. Alternatively the cell/hydrogel mixture is left in the well array and stained in situ with antigens.

Example 8. Preparation of B Cells With Magnetic Bead Bound Receptors

In some embodiments, primary B cells are transformed into antibody secreting plasma cells by incubation with IL21, IL4, and CD40L. The cells are treated with an NHS-azide heterobifunctional crosslinker and washed.

In some embodiments, Protein-G beads are prepared by activating magnetic carboxylated beads with EDC/sulfo NHS and reacting with protein G. Protein-G DBCO beads are prepared by mixing protein G beads with an NHS-DBCO heterobifunctional crosslinker. The cells are spatially separated in a microwell array. Protein G DBCO beads are added to each well. In some embodiments, soluble azide PEG and soluble protein G is also added to the wells. In some embodiments, beads with antibodies are removed from the microwell by magnetic separation, centrifugation or gravity and placed in a solution with a metabolic inhibitor such as present in many commonly available stain buffers. The antibody beads are then reacted with antigen. Alternatively the cell/bead mixture is left in the well array and stained in situ with antigens.

Example 9. Multiplexed ScFv Generation Using 5'5' Primers

In some embodiments, cDNA made from individual cells as described above is isolated in a microwell array or emulsion in a mixture containing a library of linked 5'5' primers, where one side is specific to the 5' coding frame of the heavy chain variable sequence and one side is specific to the 3' coding frame of a light chain variable sequence. Additionally the PCR mix contains Kapa Hifi polymerase and a primer library for light chain 5' variable regions and heavy chain 3' variable regions. The DNA obtained from the reaction is ligated with T4 ligase and then treated with exonuclease. This mixture is placed into a PCR with KAPA hifi for 20 cycles with the 3' heavy primer library and 5' light primer library. Following PCR this material is cloned into a suitable expression vector for production of proteins containing an ScFv fragment. Alternatively or in addition the combined ScFv DNA library is used to make a sequencing library for high throughput sequencing.

Example 10. Micropatterned Surface for Capture of Single Beads or Cells

In some embodiments, a glass surface is cleaned before spin coating with AZ4620 positive resist. In some embodiments, the surface is patterned with a chrome mask in a manner that exposes 1 um spots 50 um center to center. In some embodiments, the resist is developed and the surface is silanized with APTES, and then treated with NHS-PEG-azide. In some embodiments, the resist is stripped with acetone and DMSO, and the surface is then treated with a 10 kd PEG-silane mixed with fluorooctyl triethoxy silane to passivate the surface. Varying the ratio of PEG-silane to fluorooctyl silane will produce passivated surfaces with different qualities. In some embodiments, the ratio is 1:1000 PEG-silane:fluorooctyl silane in order make the surface slightly hydrophobic at the non-cell capture positions without contributing to non-specific interactions of cellular proteins to the passivated surface. In some embodiments, cells or beads are functionalized with NHS DBCO, washed and introduced to the array surface in a binding buffer containing 2% BSA, 1 mM EDTA and 25 mM HEPES via pipetting or syringe pump and allowed to incubate under gentle agitation or fluid flow. The array is then washed.

Example 11. Micropatterned Surface Capture of Specific Cell Types

In some embodiments, the micropatterned array from example 10 is used to capture cells displaying a specific surface marker, for example human B-cells. In some embodiments, an anti-CD19 antibody containing a DBCO moiety (an antibody functionalized with DBCO-NHS) is added to a mixture of peripheral blood mononucleocytes in a suitable stain buffer (eg PBS-BSA), washed and introduced to the array surface in a suitable binding buffer and allowed to incubate under gentle agitation or fluid flow. The array is then washed and captured B-cells are contained in the array.

Example 12. Transfer of Cells From Micropatterned Surface to Microwells for Subsequent Reactions Examples 10-11 it may be modified to spatially isolate the buffer surrounding cells or beads for additional reactions. In some embodiments, a microwell array made of PDMS with wells of size 30 um×30 um×100 um 50 um center to center deep are pre-filled with a mixture containing poly-dT beads and a weak lysis/binding mixture (for example, a mixture containing LiCl and a detergent such as 1% Triton or 0.5% Tween-20). This microwell array is placed against the micropatterned cell array from examples 10-12 in order to register 1 cell to 1 well in the array. Lysis occurs in the microwell and mRNA is captured on the poly dT beads.

Example 13. Transfer of Beads From Micropatterned Surface to Microwells for Subsequent Reactions In this embodiment, beads containing cDNA libraries and barcoded antigen tags from single cells are transferred to a microwell array as in Example 12. In some embodiments, a microwell array made of PDMS with wells of size 30 um×30 um×100 um 50 um center to center deep is prefilled containing a PCR mixture that contains primers for amplifying particular molecules of interest such as in Examples 2 and 3. The PCR reaction occurs in the microwell array.

Example 14. Spatial Confinement of Single Cells for the Capture of Antibodies on the Cellular Surface In some embodiments, single cells (cells displaying antibodies) are bound for subsequent capture on their surface. In this embodiment, cells are captured on a micropatterned surface similar to examples 10-12. In some embodiments, the spots for the micropatterned surface are derivatized with NHS-PEG-desthiobiotin and following treatment with a PEG-silane the surface is treated with a solution containing streptavidin in the cell binding buffer. The cells are functionalized with NHS-PEG-desthiobiotin and NHS-PEG-Azide before introduction to the array. Therefore a linkage between the cells and the surface is made via a desthiobiotin-streptavidin-desthiobiotin interaction. In some embodiments, a microwell array containing a mixture of protein G-DBCO is registered and placed against the cell array to spatially compartmentalize each cell for capture of antibodies secreted from the cell to its surface. After incubation, the microwell array is removed and the cells washed with a solution containing free protein G and a metabolic inhibitor. The cells may be stained with antigen in situ and released by the introduction of biotin, or released by the introduction of biotin and then stained with antigen subsequently as mentioned in previous examples.

Example 15. Transfer of Cells or Beads From Micropatterned Surface to Microwell Array In some embodiments, Example 14 is modified to transfer the cells in a registered manner to the microwell array for subsequent reactions. In this example, the cells are transferred to the microwell array. The microwell array is loaded with a solution containing biotin. Upon registration/placement of the microwell array to the micropatterned surface, the cells are released from the surface due to the displacement of desthiobiotin by biotin. The cells may be moved to the bottom of the well array by centrifugation or other means. This step may be repeated to load additional cells or beads in a similar manner so that a precise number of cells or beads are added to each position in the microwell array.

Example 16. Precise Registration of Single Bead and Single Cell in One Step

In some embodiments, a micropatterned surface with approximately 400 nM features is used to capture beads of size 1um. This is similar to Example 10 using a PEG-Azide on the surface to capture a PEG-DBCO on the beads. In some embodiments, cells are added that have been functionalized with a PEG-Azide. Since the bead sizes are much smaller than the cell diameter, approximately one cell is captured by each bead which is captured by the micropatterned surface. In this manner a precise one bead to one cell ratio on a registered grid is possible that can be used for subsequent workup. In this example the bead is also functionalized with a barcoded polydT capture probe for mRNA capture upon lysis of the single cell in a confined space, such as in Example 13. The bead/cell combo can also be released for placement in an emulsion as in Example 2.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

Those skilled in the art will recognize, or be able to ascertain using no more than routine experimentation, many equivalents to the specific embodiments of the invention described herein. Such equivalents are intended to be encompassed by the following claims.

We claim:

1. A method for making a linked nucleic acid encoding an antibody light chain and an antibody heavy chain, comprising the steps of:
   providing a plurality of host cells, wherein the plurality host cells are obtained from a subject that has a protective immune response, and wherein the host cells comprise a nucleic acid encoding an antibody heavy chain and a nucleic acid encoding an antibody light chain,
   isolating a host cell from the plurality of host cells,
   adding a lysis buffer to the host cell whereby the host cell is lysed,
   adding a linked primer as a first primer, a second primer for the antibody light chain, a third primer for the antibody heavy chain, a plurality of dNTPs, a polymerase, and an appropriate buffer to the lysed host cells, wherein the linked primer comprises a primer for the antibody heavy chain and a primer for the antibody light chain, wherein, in the linked primer, 5' end of the primer for the antibody heavy chain is linked to 5' end of the primer for the antibody light chain, wherein the linked primer and the second primer comprise a primer set for amplifying a variable region of the antibody light chain, and wherein the linked primer and the third primer comprise a primer set for amplifying a variable region of the antibody heavy chain;

amplifying a first nucleic acid encoding the variable region of the antibody light chain in the presence of the linked primer, the second primer, the dNTPs and the polymerase and amplifying a second nucleic acid encoding the variable region of the antibody heavy chain in the presence of the linker primer, the third primer, the dNTPs and the polymerase, making a circular joined nucleic acid by joining 5' end of the first nucleic acid with 3' end of the second nucleic acid and joining 3' end of the first nucleic acid with 5' end of the second nucleic acid; and making a nucleic acid encoding the antibody heavy chain and the antibody light chain by amplifying the circular joined nucleic acid.

2. The method of claim 1, wherein the linked primer pair is formed by chemically bonds.

3. The method of claim 1, wherein the host cell is in an emulsion.

4. The method of claim 1, wherein the plurality of host cells are in an array of a plurality of drops held by a surface tension.

5. The method of claim 1, wherein the protective immune response is an immune response against a viral infection.

6. The method of claim 1, wherein the protective immune response is an immune response against a bacterial pathogen.

* * * * *